US 6,897,031 B1

(12) United States Patent
Fisher et al.

(10) Patent No.: US 6,897,031 B1
(45) Date of Patent: May 24, 2005

(54) MULTIPARAMETER FACS ASSAYS TO DETECT ALTERATIONS IN EXOCYTOSIS

(75) Inventors: Joseph Fisher, Belmont, CA (US); James Lorens, Menlo Park, CA (US); Donald Payan, Hillsborough, CA (US); Alexander Rossi, San Francisco, CA (US)

(73) Assignee: Rigel Pharmaceuticals, Inc., South San Francisco, CA (US)

(*) Notice: Subject to any disclaimer, the term of this patent is extended or adjusted under 35 U.S.C. 154(b) by 0 days.

(21) Appl. No.: 09/062,330

(22) Filed: Apr. 17, 1998

(51) Int. Cl.[7] .................................. G01N 33/567
(52) U.S. Cl. .................. 435/7.21; 424/1.41; 424/406; 435/7.2; 436/164; 436/172; 356/485; 356/492; 356/495
(58) Field of Search ...................... 435/6, 7.1–7.6, 435/69.1, 7, 7.21, 21, 29, 40.5, 772, 40.51, 288.3, 288.4, 962, 808, 325, 375, 372.3, 240.1, 172.3, 973, 974, 7.4, 320.1; 531/23.1; 514/2, 12–19, 300, 169, 9, 10, 14, 31; 436/546, 172, 518, 800, 809, 811, 532, 175, 533, 534, 805, 63, 94; 530/350, 402; 424/93.21

(56) References Cited

U.S. PATENT DOCUMENTS

| | | | |
|---|---|---|---|
| 4,304,720 A | | 12/1981 | Dean et al. ............... 260/335 |
| 5,073,497 A | * | 12/1991 | Schwartz .................... 436/8 |
| 5,436,128 A | * | 7/1995 | Harpold et al. ............ 435/6 |
| 5,567,627 A | * | 10/1996 | Lehnen ..................... 436/518 |
| 5,646,001 A | * | 7/1997 | Terstappen et al. ...... 435/7.21 |
| 5,790,710 A | * | 8/1998 | Price et al. ............... 382/255 |
| 5,955,275 A | * | 9/1999 | Kamb ....................... 435/6 |
| 5,981,180 A | * | 11/1999 | Chandler et al. .......... 435/6 |
| 5,981,200 A | * | 11/1999 | Tsien et al. ............... 435/7.4 |
| 6,135,941 A | * | 10/2000 | Hillman et al. ........... 536/23.1 |

FOREIGN PATENT DOCUMENTS

| | | | | |
|---|---|---|---|---|
| EP | 0 415 695 | 3/1991 | ......... | G01N/33/577 |
| EP | 0 469 632 | 2/1992 | ............ | C12Q/1/18 |
| WO | 91/02085 | 2/1991 | ............ | C12Q/1/02 |
| WO | WO 97/27212 | * 7/1997 | | |
| WO | 98/58085 | 12/1998 | ............ | C12Q/1/68 |

OTHER PUBLICATIONS

Betz et al., "Imaging exocytosis and endocytosis.", Current Opinion in Neurobiology, 6:365–371, 1996.*
Taylor et al., "The new vision of light microscopy.", American Scientist, vol. 80, pp. 322–335, 1992.*
McHugh, Immunochemica, vol. 5., No. 1., pp. 1–6, 1991.*
Rizzuto et al., "Chimeric green fluorescent protein as a tool for visualizing subcellular organelles in living cells.", Current Biology, vol. 5, No. 6, 1995.*
Proffitt et al., "A fluorescence digital image microscopy system for quantifying relativr cell numbers in tissue culture plates.", Cytometry, vol. 24, pp. 204–213, 1996.*

(Continued)

*Primary Examiner*—Long V. Le
*Assistant Examiner*—Nelson Yang
(74) *Attorney, Agent, or Firm*—Lahive & Cockfield, LLP; DeAnn F. Smith

(57) ABSTRACT

Described is a method for screening for alterations in exocytosis of a population of cells. The cells are sorted by a FACS machine by assaying for alterations in at least three of the properties selected from the group consisting of light scattering, fluorescent dye uptake, fluorescent dye release, annexin granule binding, surface granule enzyme activity, and the quantity of granule specific proteins. Methods for screening for bioactive agents capable of modulating exocytosis in a cell are also described. The methods provide for reduced background and increased specificity without increasing the time or steps involved in assaying for exocytosis.

36 Claims, 12 Drawing Sheets

OTHER PUBLICATIONS

Hide et al.,degranulation of individual mast cells in response to Ca2+ and guanine nucleotides: An all or none event. The Journal of Cell Biology,vol. 123, 1993, pp. 585–593.*

Liu et al. "Protein phosphorylation events in exocytosis and endocytosis", Clinical and Experimental Pharmacolgy and Phsiology, 1997, 24, 611–618.*

Kline et al, Repetitive calcium transients and the role of calcium in exocytosis and cell cycle activation in the mouse egg, 1992, 149(1), 80–89.*

Mizuno et al, Altered bcl–2 and bax expression and intracellular Ca2+ signaling in apoptosis of pancreatic cells and the impairment of glucose induced insulin secretion, Mar. 1998, Endocrin, 139(3), 1429–1439.*

Hurtley, Recycling of a secretory granule membrane protein after stimulated secretion, 1993, J Cell Sc, 106, 649–656.*

Perretti et al, Investigation of rat mast cell degranulation using flow cytometry, 1990, J Pharm Meth, 23, 187–194.*

Smyrnis et al, Fluorescence–activated cell sorter analysis of bulk isolated porcine oligodendrocytes, 1986, J Neuroimm, 13, 47–60.*

Weaver, Gel microdroplets for microbial measurement and screening: basic principles, 1986, Biotech and Bioeng Symp, 17, 186–195.*

Lawson et al, Molecular events during membrane fusion: A study of exocytosis in rat peritoneal mast cells, 1977, J Cell Bio, 72, 242–259.*

Powell et al, Gel microdroplets and flow cytometry: rapid determination of antibody secretion by individual cells within a cell population, 1990, Biotech, 8, 333–337.*

Berlin, G., et al., "Mast Cell Secretion Rapid Sealing of Exocytotic Cavities Demonstrated by Cytofluorometry," Int. Archs. Allergy appl. Immun., 73:256–262 (1984).

Betz, W.J., et al., "Imaging Exocytosis and Endocytosis," Current Opinion in Neurobiology, 6:365–371 (1996).

Deurs, B., et al., "Kinetics of Pinocytosis Studied by Flow Cytometry," European Journal of Cell Biology, 34:96–102 (1984).

Haller, T., et al., "The Lysosomal Compartment as Intracellular Calcium Store in MDCK Cells: A Possible Involvement in InsP$_3$—Mediated Ca$^{2+}$ Release," Cell Calcium, 19(2):157–165 (1996).

Hide, I., et al., "Degranulation of Individual Mast Cells in Response to Ca$^{2+}$ and Guanine Nucleotides: An All–or–None Event," The Journal of Cell Biology, 123(3):585–593 (1993).

Miyawaki, A., et al., "Fluorescent Indicators for Ca$^{2+}$Based on Green Fluorescent Proteins and Calmodulin," Nature, 388(28):882–887 (1997).

Perretti, M., et al., "Investigation of Rat Mast Cell Degranulation Using Flow Cytometry," Journal of Pharmacological Methods, 23:187–194 (1990).

Wendland, B., et al., "A Novel Fluorescence–Activated Cell Sorter–Based Screen for Yeast Endocytosis Mutants Identifies a Yeast Homologue of Mammalian eps15," The Journal of Cell Biology, 135(6) Part 1:1485–1500 (Dec. 1996).

Xu, X., et al., "Detection of Programmed Cell Death Using Fluorescence Energy Transfer," Nucleic Acids Research, 26(8):2034–2035 (1998).

Beuth, J. et al., "Determination of lectin–dependent alterations of cellular parameters by immunophenotyping during adjuvant lectin application," *Lectins Glycobiol.* (1993) Gabius and Gabius, eds. (1993) Springer–Verlag, Berlin, Germany, pp. 396–401.

Jia–Ping, et al. "Multi–parameter sorting technique in flow cytometry." *Chinese Journal of Physical Medicine.* 1995;17 (3):168–171.

Ryan et al. "Improved detection of rare CALLA–positive cells in peripheral blood using multiparameter flow cytometry." *J. Immunol. Meth.* 1984;74:115–128.

* cited by examiner

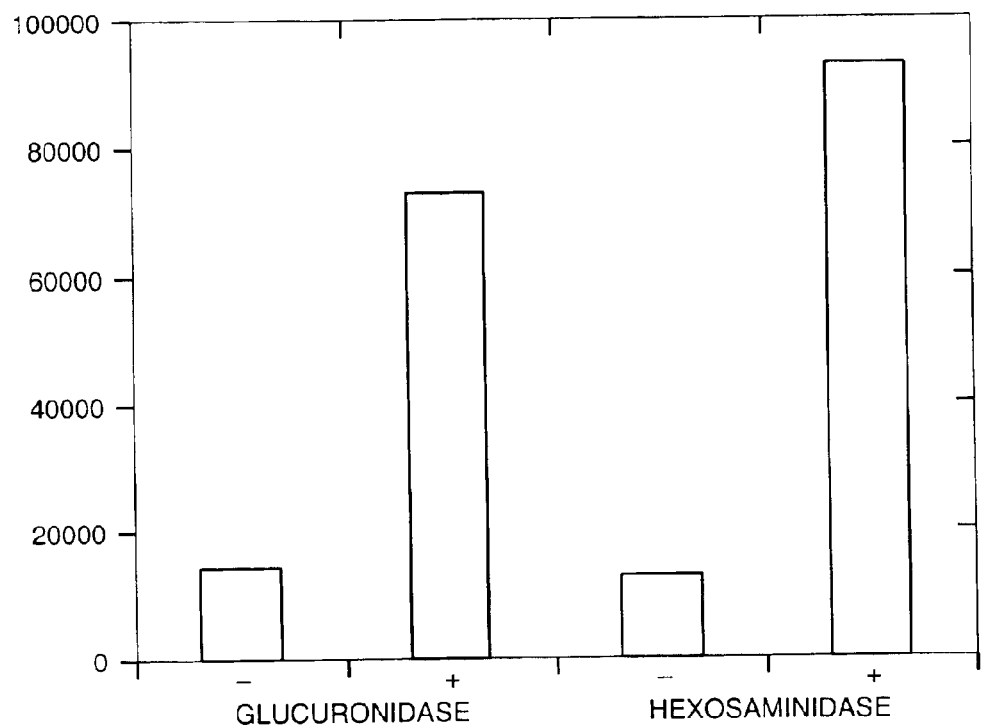
FIG._1A
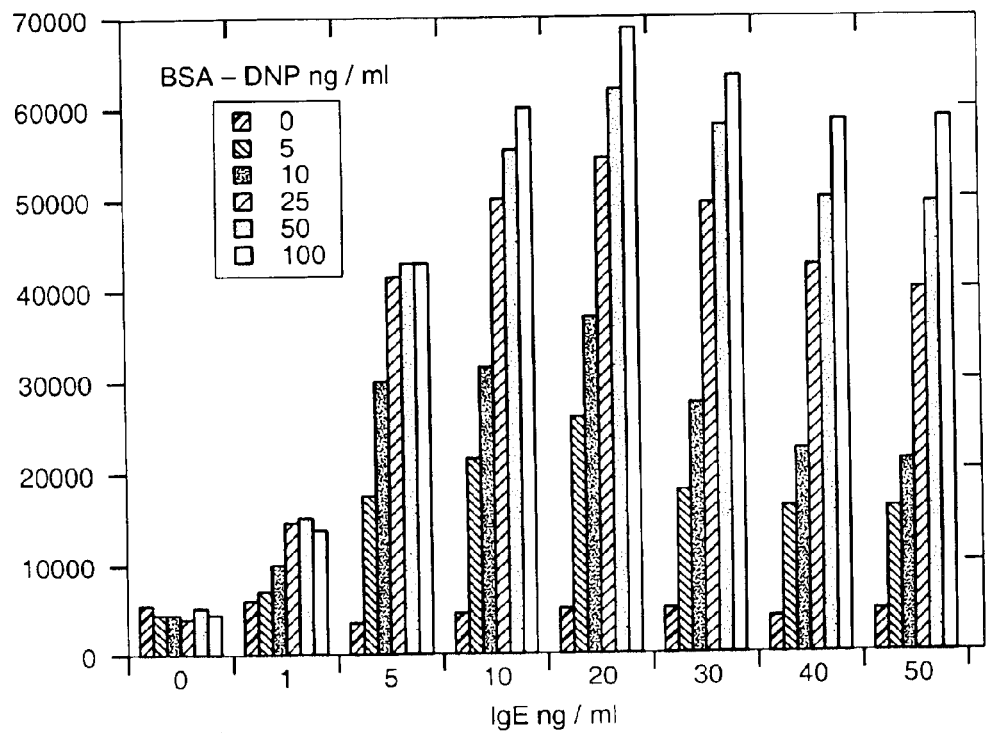
FIG._1B

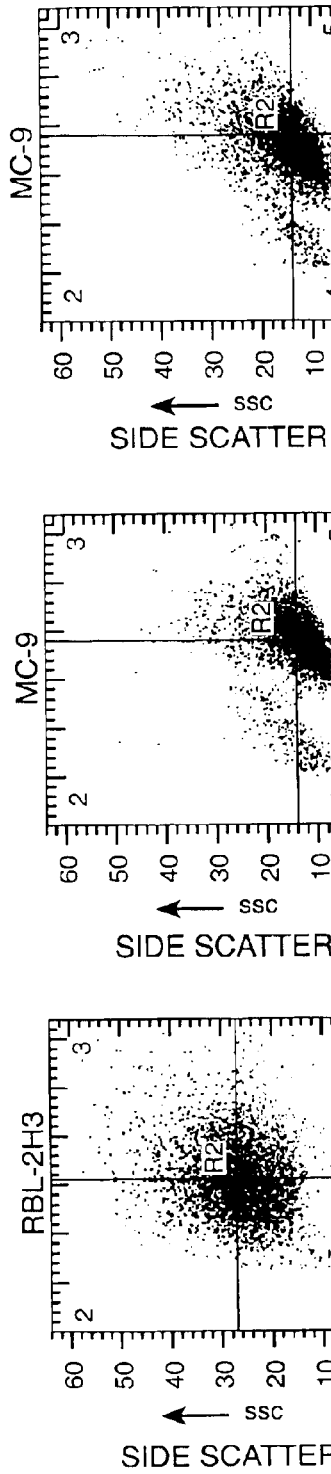
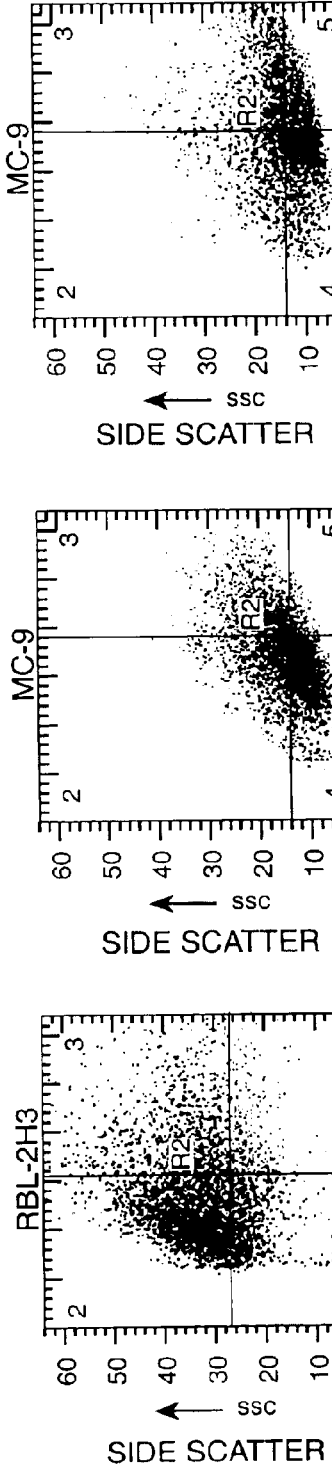
FIG._2A FIG._2B FIG._2C FIG._2D FIG._2E FIG._2F

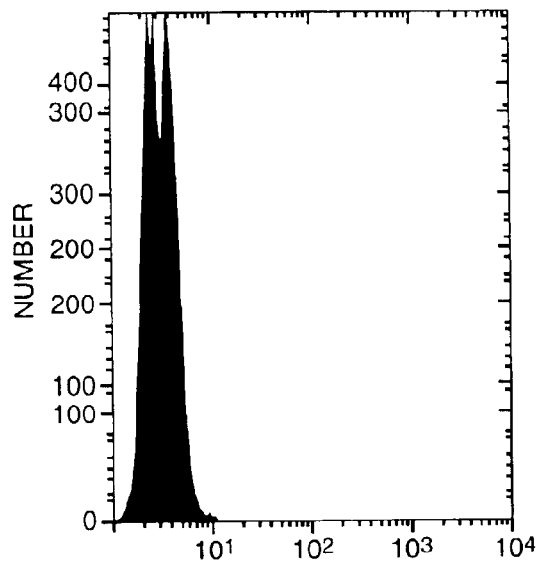
FIG._3A
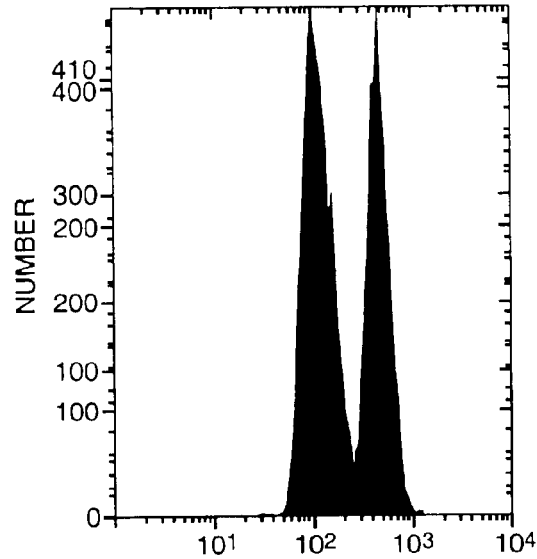
FIG._3B
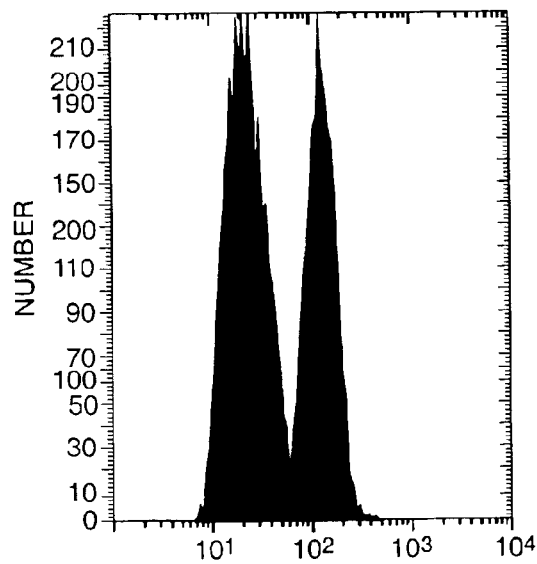
FIG._3C
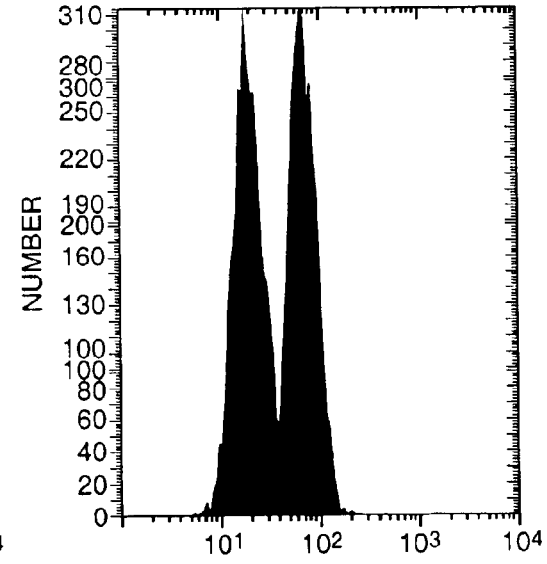
FIG._3D

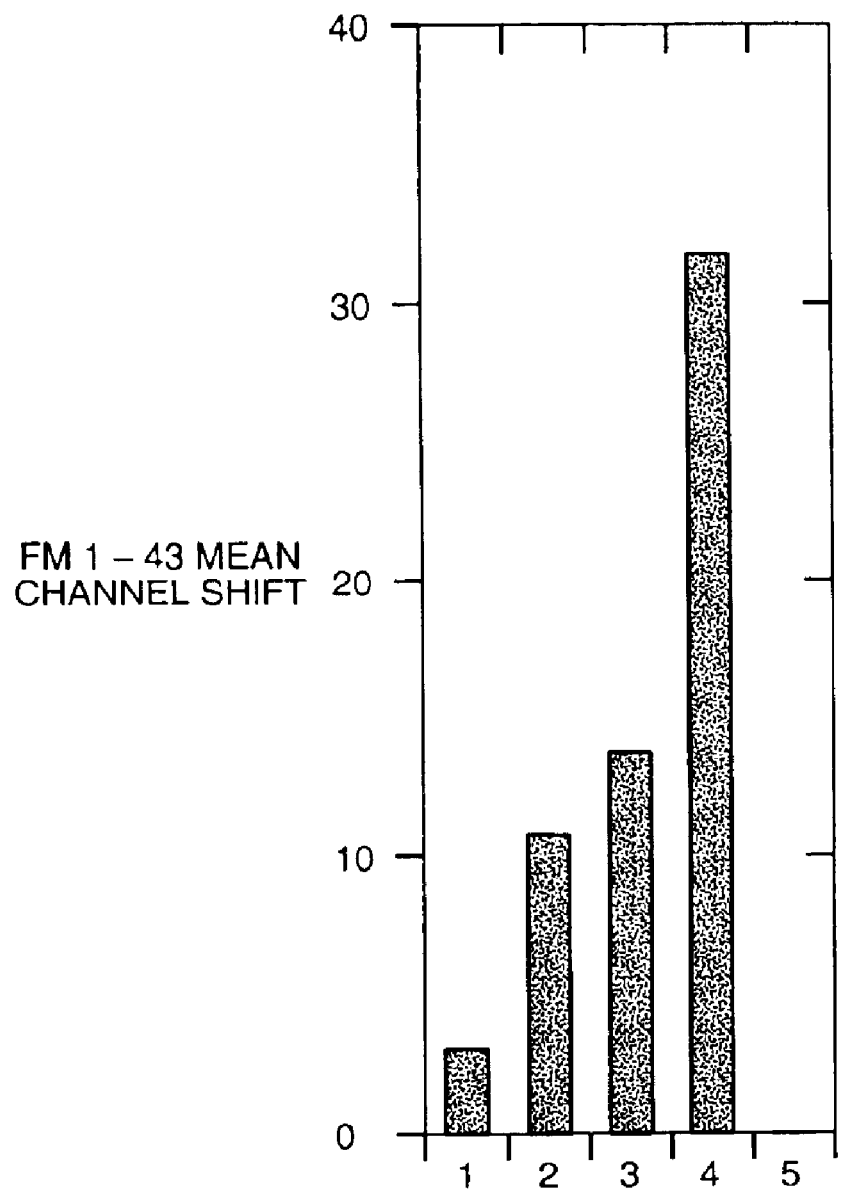
FIG._3E

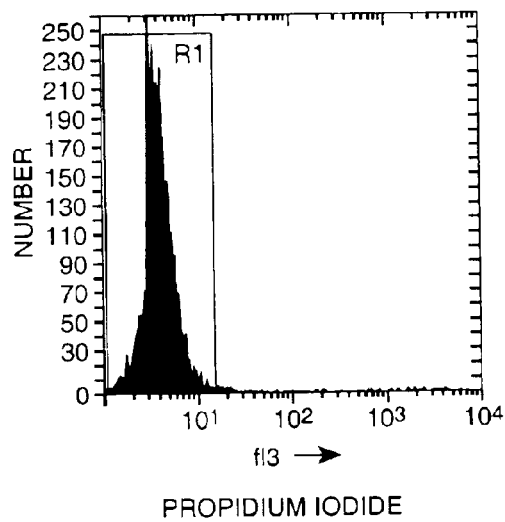
FIG._4A
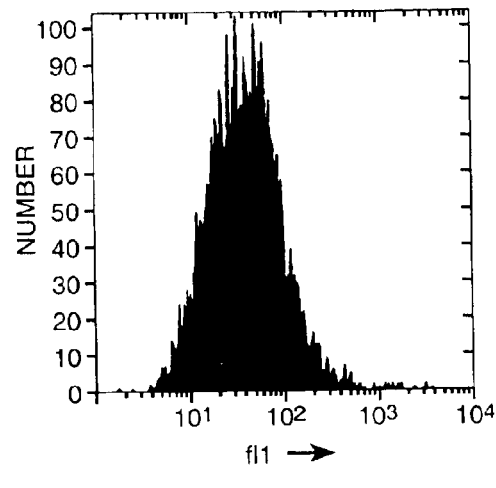
FIG._4B
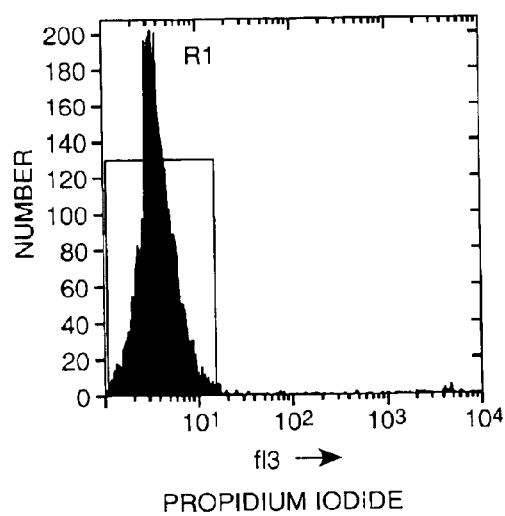
FIG._4C
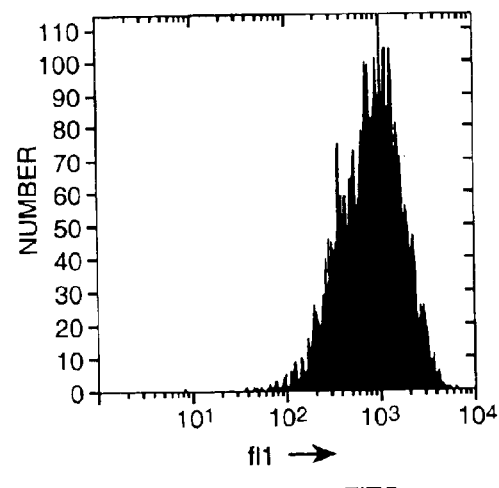
FIG._4D

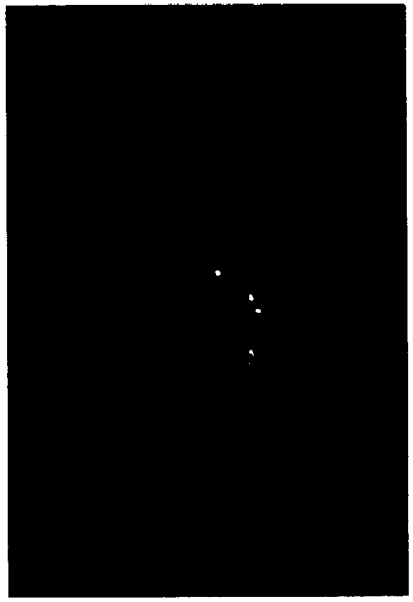
FIG._5B
FIG._5D
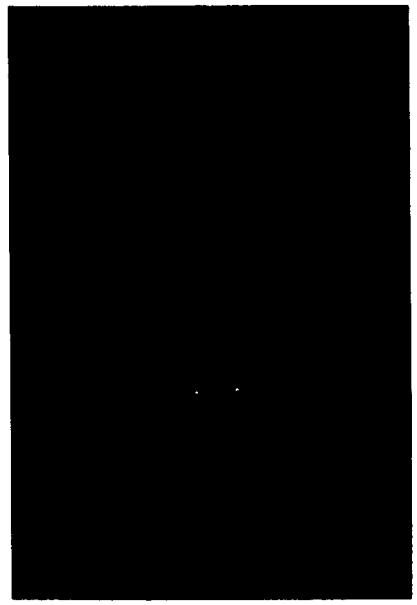
FIG._5A
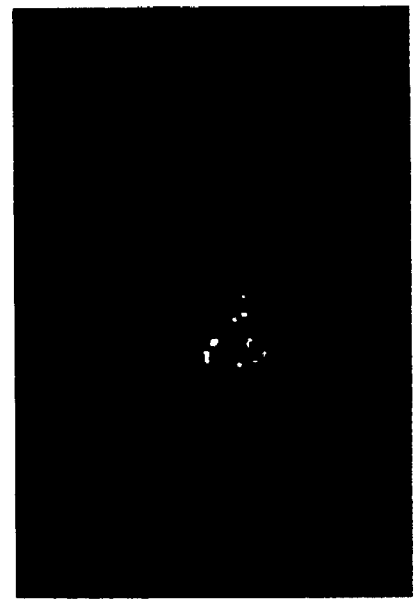
FIG._5C

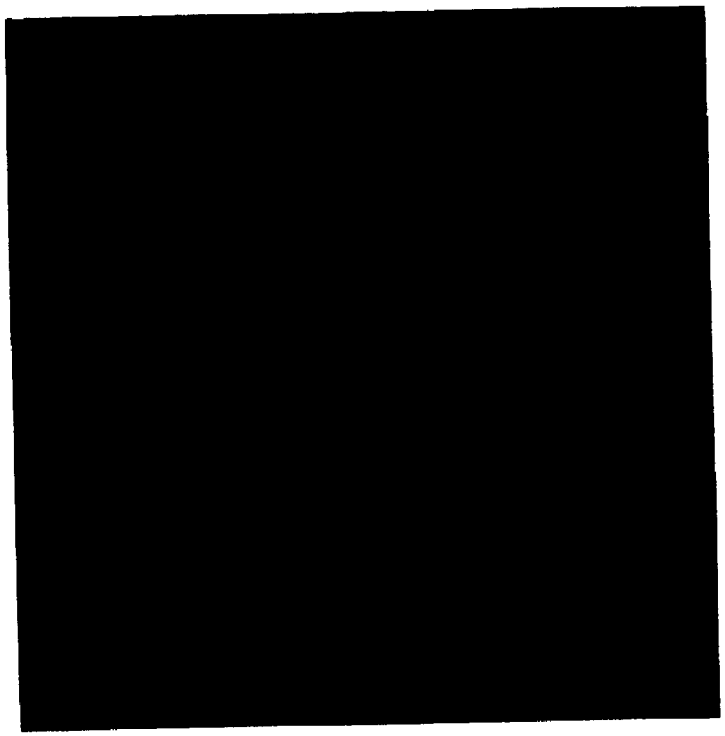
FIG._6A
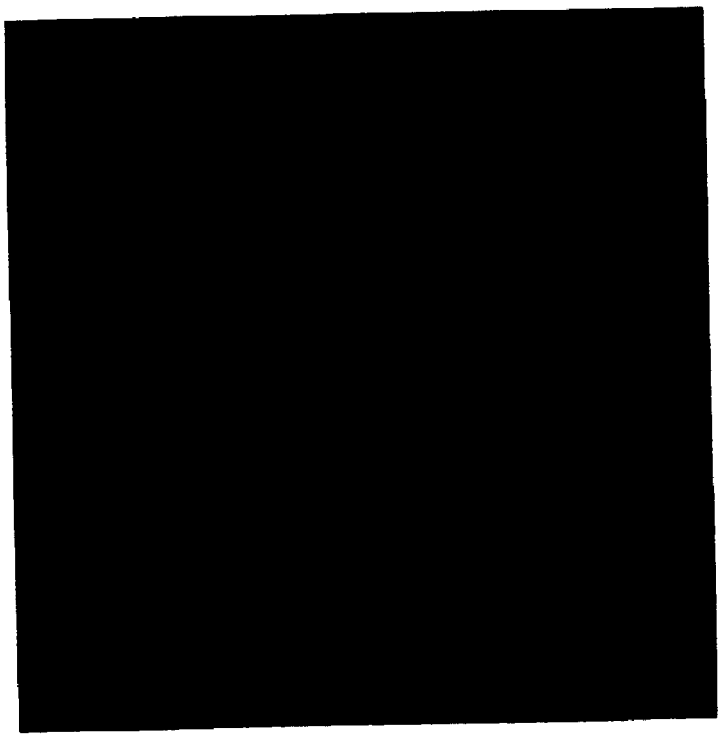
FIG._6B

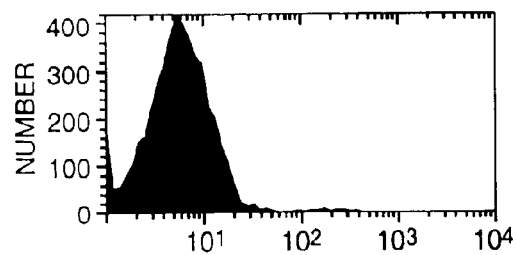 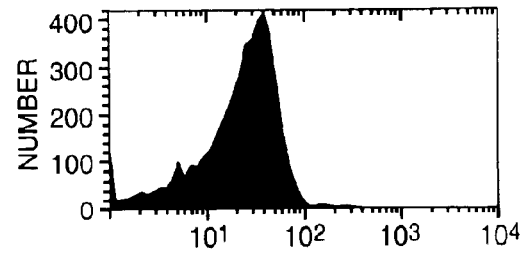
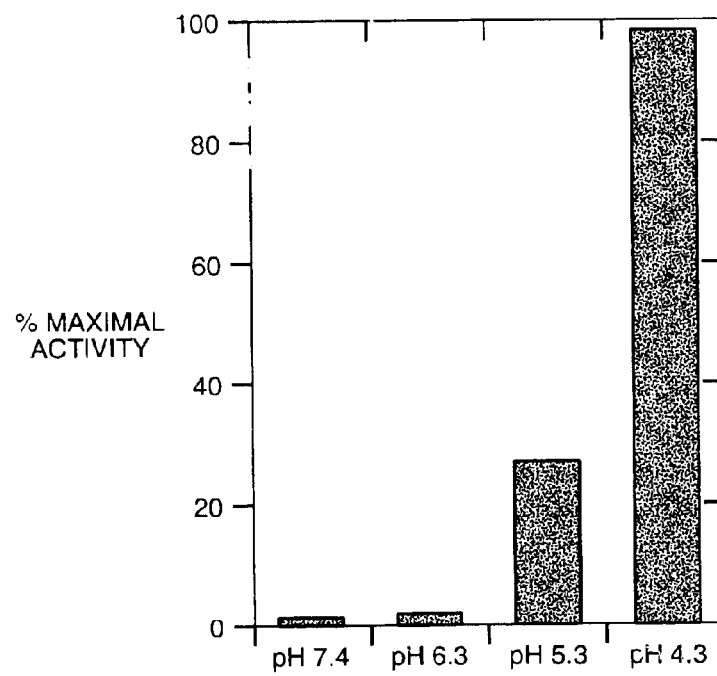
FIG._7A  FIG._7B  FIG._7C

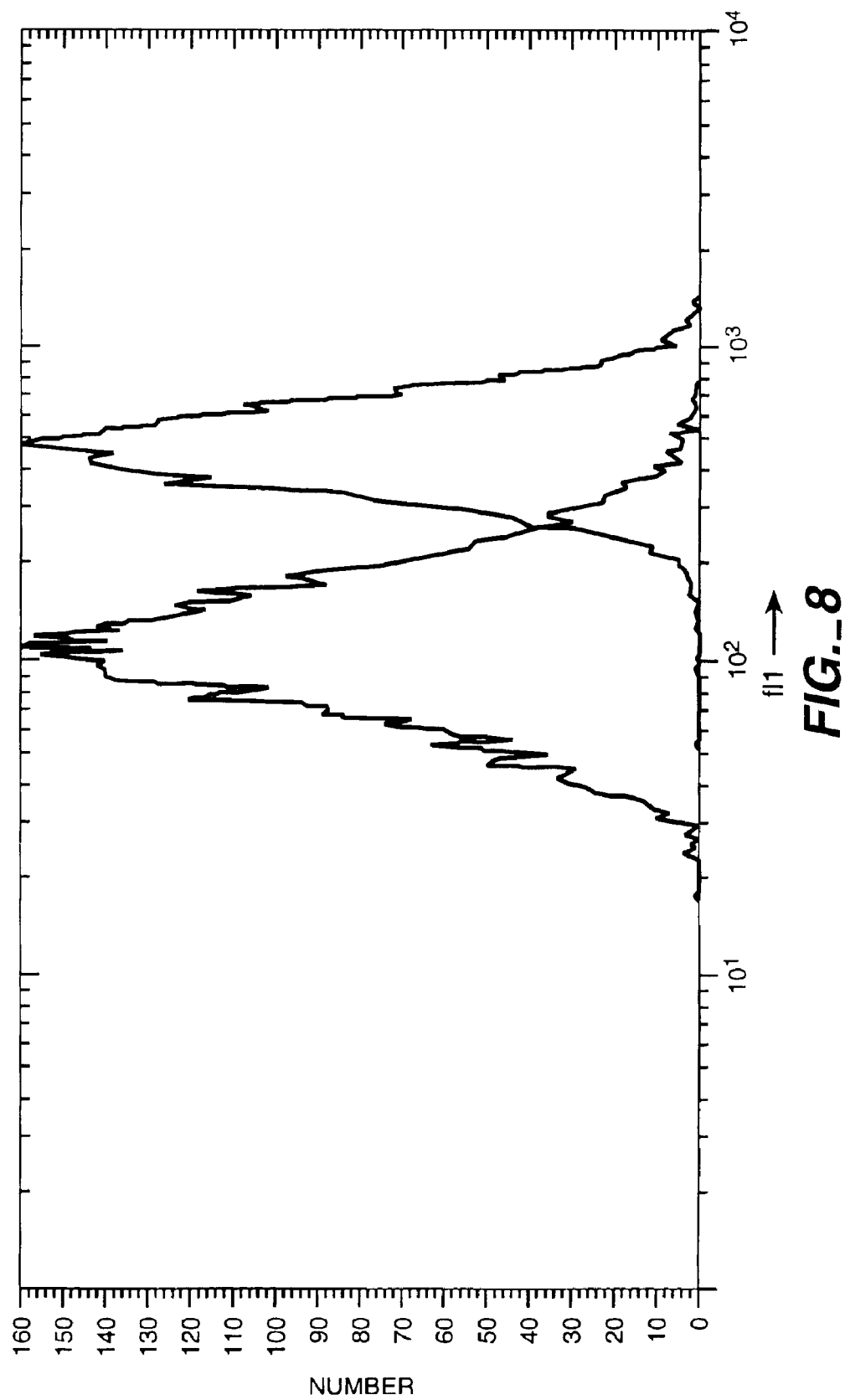
FIG._8

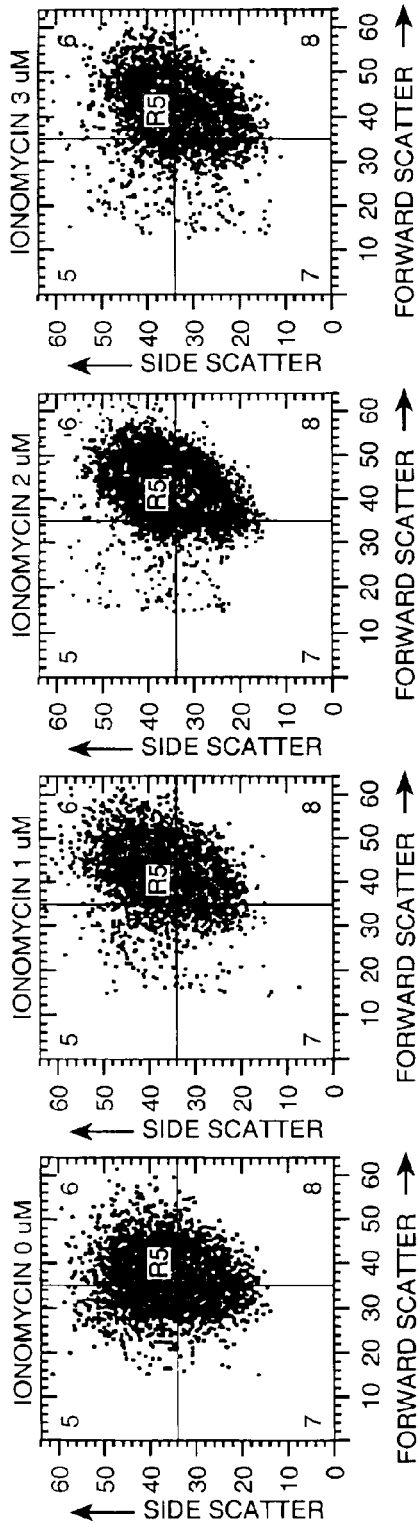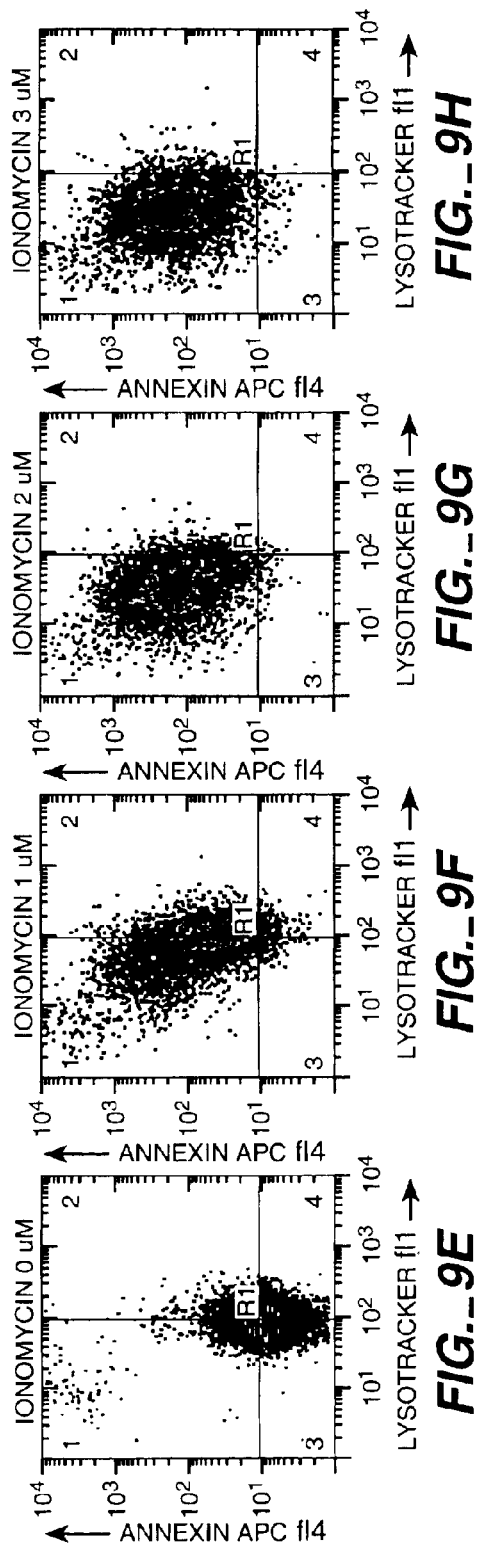

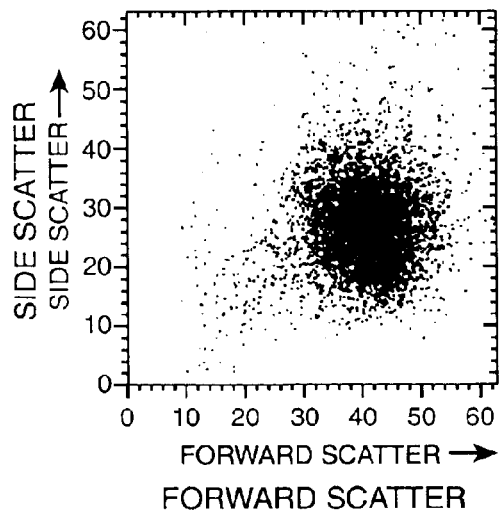
FIG._10A
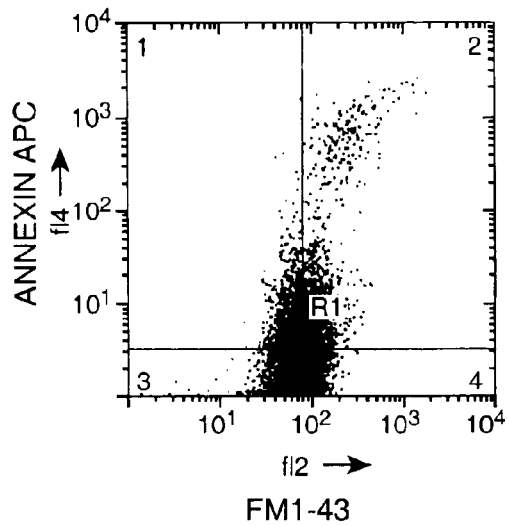
FIG._10B
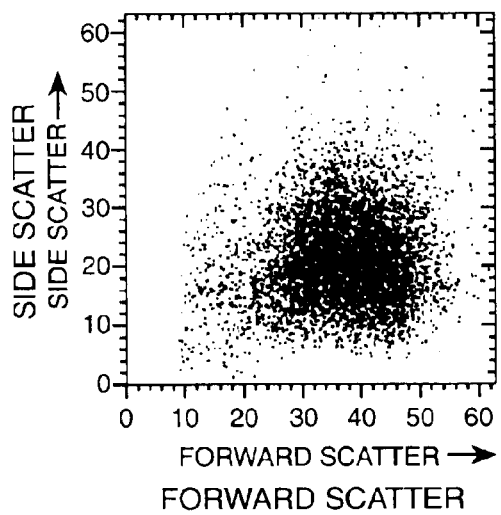
FIG._10C
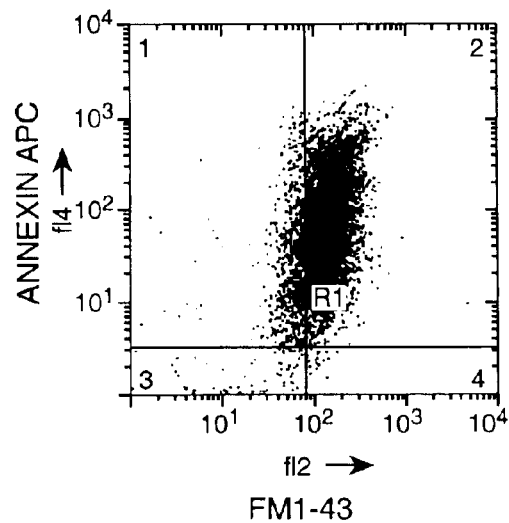
FIG._10D

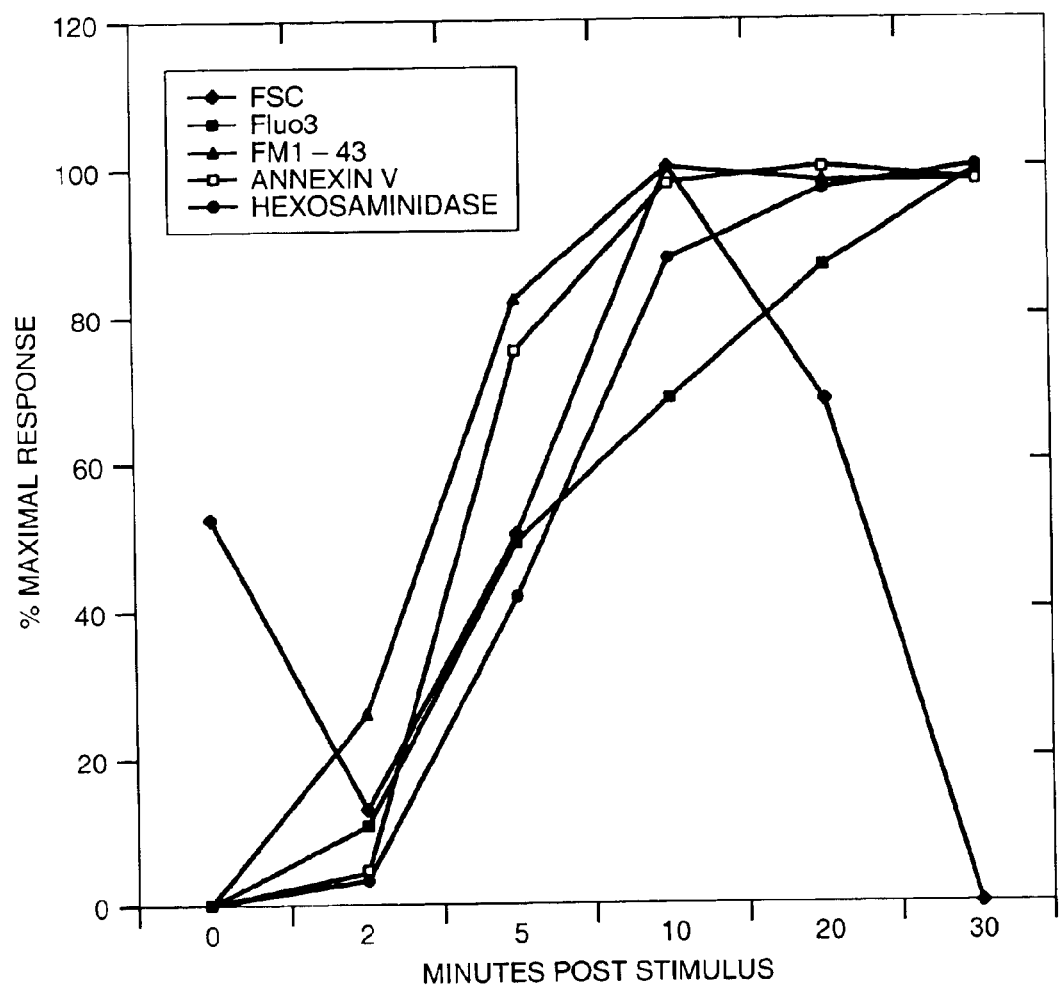
FIG._11

SEQUENCE LISTING

<160> NUMBER OF SEQ ID NOS: 39

<210> SEQ ID NO 1
<211> LENGTH: 61
<212> TYPE: PRT
<213> ORGANISM: Artificial sequence
<220> FEATURE:
<223> OTHER INFORMATION: coiled-coil presentation structure

<400> SEQUENCE: 1

Met Gly Cys Ala Ala Leu Glu Ser Glu Val Ser Ala Leu Glu Ser Glu
1               5                   10                  15

Val Ala Ser Leu Glu Ser Glu Val Ala Ala Leu Gly Arg Gly Asp Met
                20                  25                  30

Pro Leu Ala Ala Val Lys Ser Lys Leu Ser Ala Val Lys Ser Lys Leu
            35                  40                  45

Ala Ser Val Lys Ser Lys Leu Ala Ala Cys Gly Pro Pro
        50                  55                  60

<210> SEQ ID NO 2
<211> LENGTH: 69
<212> TYPE: PRT
<213> ORGANISM: Artificial sequence
<220> FEATURE:
<223> OTHER INFORMATION: minibody presentation structure

<400> SEQUENCE: 2

Met Gly Arg Asn Ser Gln Ala Thr Ser Gly Phe Thr Phe Ser His Phe
1               5                   10                  15

Tyr Met Glu Trp Val Arg Gly Gly Glu Tyr Ile Ala Ala Ser Arg His

-continued

```
                    20                  25                  30
Lys His Asn Lys Tyr Thr Thr Glu Tyr Ser Ala Ser Val Lys Gly Arg
             35                  40                  45

Tyr Ile Val Ser Arg Asp Thr Ser Gln Ser Ile Leu Tyr Leu Gln Lys
     50                  55                  60

Lys Lys Gly Pro Pro
65

<210> SEQ ID NO 3
<211> LENGTH: 7
<212> TYPE: PRT
<213> ORGANISM: Simian virus 40

<400> SEQUENCE: 3

Pro Lys Lys Lys Arg Lys Val
1               5

<210> SEQ ID NO 4
<211> LENGTH: 6
<212> TYPE: PRT
<213> ORGANISM: Homo sapiens

<400> SEQUENCE: 4

Ala Arg Arg Arg Arg Pro
1               5

<210> SEQ ID NO 5
<211> LENGTH: 10
<212> TYPE: PRT
<213> ORGANISM: Mus musculus

<400> SEQUENCE: 5

Glu Glu Val Gln Arg Lys Arg Gln Lys Leu
1               5                  10

<210> SEQ ID NO 6
<211> LENGTH: 9
<212> TYPE: PRT
<213> ORGANISM: Mus musculus

<400> SEQUENCE: 6

Glu Glu Lys Arg Lys Arg Thr Tyr Glu
1               5

<210> SEQ ID NO 7
<211> LENGTH: 20
<212> TYPE: PRT
<213> ORGANISM: Xenopus laevis

<400> SEQUENCE: 7

Ala Val Lys Arg Pro Ala Ala Thr Lys Lys Ala Gly Gln Ala Lys Lys
1               5                  10                  15

Lys Lys Leu Asp
            20

<210> SEQ ID NO 8
<211> LENGTH: 31
<212> TYPE: PRT
<213> ORGANISM: Mus musculus

<400> SEQUENCE: 8

Met Ala Ser Pro Leu Thr Arg Phe Leu Ser Leu Asn Leu Leu Leu Leu
1               5                  10                  15
```

-continued

Gly Glu Ser Ile Leu Gly Ser Gly Ala Lys Pro Gln Ala Pro
            20              25              30

<210> SEQ ID NO 9
<211> LENGTH: 21
<212> TYPE: PRT
<213> ORGANISM: Homo sapiens

<400> SEQUENCE: 9

Met Ser Ser Phe Gly Tyr Arg Thr Leu Thr Val Ala Leu Phe Thr Leu
1               5                   10                  15

Ile Cys Cys Pro Gly
            20

<210> SEQ ID NO 10
<211> LENGTH: 51
<212> TYPE: PRT
<213> ORGANISM: Mus musculus

<400> SEQUENCE: 10

Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Leu Ser Leu Ile Ile Thr Leu Ile Cys Tyr
            35                  40                  45

His Ser Arg
    50

<210> SEQ ID NO 11
<211> LENGTH: 33
<212> TYPE: PRT
<213> ORGANISM: Homo sapiens

<400> SEQUENCE: 11

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 12
<211> LENGTH: 37
<212> TYPE: PRT
<213> ORGANISM: Rattus sp.

<400> SEQUENCE: 12

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 13
<211> LENGTH: 14
<212> TYPE: PRT
<213> ORGANISM: Gallus gallus

<400> SEQUENCE: 13

```
Met Gly Ser Ser Lys Ser Lys Pro Lys Asp Pro Ser Gln Arg
1               5                   10
```

<210> SEQ ID NO 14
<211> LENGTH: 26
<212> TYPE: PRT
<213> ORGANISM: Homo sapiens

<400> SEQUENCE: 14

```
Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25
```

<210> SEQ ID NO 15
<211> LENGTH: 20
<212> TYPE: PRT
<213> ORGANISM: Rattus norvegicus

<400> SEQUENCE: 15

```
Lys Gln Phe Arg Asn Cys Met Leu Thr Ser Leu Cys Cys Gly Lys Asn
1               5                   10                  15

Pro Leu Gly Asp
            20
```

<210> SEQ ID NO 16
<211> LENGTH: 19
<212> TYPE: PRT
<213> ORGANISM: Homo sapiens

<400> SEQUENCE: 16

```
Leu Asn Pro Pro Asp Glu Ser Gly Pro Gly Cys Met Ser Cys Lys Cys
1               5                   10                  15

Val Leu Ser
```

<210> SEQ ID NO 17
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 17

```
Lys Phe Glu Arg Gln
1               5
```

<210> SEQ ID NO 18
<211> LENGTH: 36
<212> TYPE: PRT
<213> ORGANISM: Cricetulus griseus

<400> SEQUENCE: 18

```
Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35
```

<210> SEQ ID NO 19
<211> LENGTH: 35
<212> TYPE: PRT
<213> ORGANISM: Homo sapiens -continued

<400> SEQUENCE: 19

Leu Val Pro Ile Ala Val Gly Ala Ala Leu Ala Gly Val Leu Ile Leu
1               5                   10                  15

Val Leu Leu Ala Tyr Phe Ile Gly Leu Lys His His Ala Gly Tyr
            20                  25                  30

Glu Gln Phe
        35

<210> SEQ ID NO 20
<211> LENGTH: 27
<212> TYPE: PRT
<213> ORGANISM: Saccharomyces cerevisiae

<400> SEQUENCE: 20

Met Leu Arg Thr Ser Ser Leu Phe Thr Arg Val Gln Pro Ser Leu
1               5                   10                  15

Phe Ser Arg Asn Ile Leu Arg Leu Gln Ser Thr
            20                  25

<210> SEQ ID NO 21
<211> LENGTH: 25
<212> TYPE: PRT
<213> ORGANISM: Saccharomyces cerevisiae

<400> SEQUENCE: 21

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 22
<211> LENGTH: 64
<212> TYPE: PRT
<213> ORGANISM: Saccharomyces cerevisiae

<400> SEQUENCE: 22

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 23
<211> LENGTH: 41
<212> TYPE: PRT
<213> ORGANISM: Saccharomyces cerevisiae

<400> SEQUENCE: 23

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 24

```
<211> LENGTH: 4
<212> TYPE: PRT
<213> ORGANISM: Homo sapiens

<400> SEQUENCE: 24

Lys Asp Glu Leu
1

<210> SEQ ID NO 25
<211> LENGTH: 15
<212> TYPE: PRT
<213> ORGANISM: unidentified adenovirus

<400> SEQUENCE: 25

Leu Tyr Leu Ser Arg Arg Ser Phe Ile Asp Glu Lys Lys Met Pro
1               5                   10                  15

<210> SEQ ID NO 26
<211> LENGTH: 19
<212> TYPE: PRT
<213> ORGANISM: Homo sapiens

<400> SEQUENCE: 26

Leu Asn Pro Pro Asp Glu Ser Gly Pro Gly Cys Met Ser Cys Lys Cys
1               5                   10                  15

Val Leu Ser

<210> SEQ ID NO 27
<211> LENGTH: 15
<212> TYPE: PRT
<213> ORGANISM: Homo sapiens

<400> SEQUENCE: 27

Leu Thr Glu Pro Thr Gln Pro Thr Arg Asn Gln Cys Cys Ser Asn
1               5                   10                  15

<210> SEQ ID NO 28
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 28

Arg Thr Ala Leu Gly Asp Ile Gly Asn
1               5

<210> SEQ ID NO 29
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 29

Met Tyr Arg Met Gln Leu Leu Ser Cys Ile Ala Leu Ser Leu Ala Leu
1               5                   10                  15

Val Thr Asn Ser
            20

<210> SEQ ID NO 30
<211> LENGTH: 29
<212> TYPE: PRT
<213> ORGANISM: Homo sapiens
```

```
<400> SEQUENCE: 30

Met Ala Thr Gly Ser Arg Thr Ser Leu Leu Ala Phe Gly Leu Leu
1               5                   10                  15

Cys Leu Pro Trp Leu Gln Glu Gly Ser Ala Phe Pro Thr
                20                  25

<210> SEQ ID NO 31
<211> LENGTH: 27
<212> TYPE: PRT
<213> ORGANISM: Homo sapiens

<400> SEQUENCE: 31

Met Ala Leu Trp Met Arg Leu Leu Pro Leu Leu Ala Leu Leu Ala Leu
1               5                   10                  15

Trp Gly Pro Asp Pro Ala Ala Phe Val Asn
                20                  25

<210> SEQ ID NO 32
<211> LENGTH: 18
<212> TYPE: PRT
<213> ORGANISM: Influenza virus

<400> SEQUENCE: 32

Met Lys Ala Lys Leu Leu Val Leu Leu Tyr Ala Phe Val Ala Gly Asp
1               5                   10                  15

Gln Ile

<210> SEQ ID NO 33
<211> LENGTH: 24
<212> TYPE: PRT
<213> ORGANISM: Unknown
<220> FEATURE:
<223> OTHER INFORMATION: signal sequence from Interleukin-4

<400> SEQUENCE: 33

Met Gly Leu Thr Ser Gln Leu Leu Pro Pro Leu Phe Phe Leu Leu Ala
1               5                   10                  15

Cys Ala Gly Asn Phe Val His Gly
                20

<210> SEQ ID NO 34
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be any amino acid

<400> SEQUENCE: 34

Met Gly Xaa Xaa Xaa Xaa Gly Gly Pro Pro
1               5                   10

<210> SEQ ID NO 35
<211> LENGTH: 5
<212> TYPE: PRT
<213> ORGANISM: Artificial sequence
<220> FEATURE:
<223> OTHER INFORMATION: linker consensus sequence

<400> SEQUENCE: 35

Gly Ser Gly Gly Ser
1               5
```

-continued

<210> SEQ ID NO 36
<211> LENGTH: 4
<212> TYPE: PRT
<213> ORGANISM: Artificial sequence
<220> FEATURE:
<223> OTHER INFORMATION: linker consensus sequence

<400> SEQUENCE: 36

Gly Gly Gly Ser
1

<210> SEQ ID NO 37
<211> LENGTH: 368
<212> TYPE: PRT
<213> ORGANISM: Artificial sequence
<220> FEATURE:
<223> OTHER INFORMATION: synthetic construct

<400> SEQUENCE: 37

Met Gly Ser Ala Thr Ala Ala Thr Val Pro Pro Ala Ala Pro Ala Gly
1               5                   10                  15

Glu Gly Gly Pro Pro Ala Pro Pro Pro Asn Leu Thr Ser Asn Arg Arg
                20                  25                  30

Leu Gln Gln Thr Gln Ala Gln Val Asp Glu Val Val Asp Ile Met Arg
            35                  40                  45

Val Asn Val Asp Lys Val Leu Glu Arg Asp Gln Lys Leu Ser Glu Leu
        50                  55                  60

Asp Asp Arg Ala Asp Ala Leu Gln Ala Gly Ala Ser Gln Phe Glu Thr
65                  70                  75                  80

Ser Ala Ala Lys Leu Lys Arg Lys Tyr Trp Trp Lys Asn Leu Lys Met
                85                  90                  95

Met Ile Ile Leu Gly Val Ile Cys Ala Ile Ile Leu Ile Ile Ile Ile
                100                 105                 110

Val Tyr Phe Ser Thr Gly Ser Gly Ser Gly Ser Gly Ser Gly Ser Gly
            115                 120                 125

Pro Val Ser Lys Gly Glu Glu Leu Phe Thr Gly Val Val Pro Ile Leu
        130                 135                 140

Val Glu Leu Asp Gly Asp Val Asn Gly His Lys Phe Ser Val Ser Gly
145                 150                 155                 160

Glu Gly Glu Gly Asp Ala Thr Tyr Gly Lys Leu Thr Leu Lys Phe Ile
                165                 170                 175

Cys Thr Thr Gly Lys Leu Pro Val Pro Trp Pro Thr Leu Val Thr Thr
                180                 185                 190

Leu Thr His Gly Val Gln Cys Phe Ser Arg Tyr Pro Asp His Met Lys
            195                 200                 205

Gln His Asp Phe Phe Lys Ser Ala Met Pro Glu Gly Tyr Val Gln Glu
        210                 215                 220

Arg Thr Ile Phe Phe Lys Asp Asp Gly Asn Tyr Lys Thr Arg Ala Glu
225                 230                 235                 240

Val Lys Phe Glu Gly Asp Thr Leu Val Asn Arg Ile Glu Leu Lys Gly
                245                 250                 255

Ile Asp Phe Lys Glu Asp Gly Asn Ile Leu Gly His Lys Leu Glu Tyr
                260                 265                 270

Asn Phe Asn Ser His Asn Val Tyr Ile Met Ala Asp Lys Gln Lys Asn
            275                 280                 285

```
Gly Ile Lys Val Asn Phe Lys Ile Arg His Asn Ile Glu Asp Gly Ser
        290                 295                 300

Val Gln Leu Ala Asp His Tyr Gln Gln Asn Thr Pro Ile Gly Asp Gly
305                 310                 315                 320

Pro Val Leu Leu Pro Asp Asn His Tyr Leu Ser Thr Gln Ser Ala Leu
                325                 330                 335

Ser Lys Asp Pro Asn Glu Lys Arg Asp His Met Val Leu Leu Glu Phe
                340                 345                 350

Val Thr Ala Ala Gly Ile Thr Leu Gly Met Asp Glu Leu Tyr Lys Glx
                355                 360                 365
```

<210> SEQ ID NO 38
<211> LENGTH: 481
<212> TYPE: PRT
<213> ORGANISM: Artificial sequence
<220> FEATURE:
<223> OTHER INFORMATION: synthetic construct

<400> SEQUENCE: 38

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
        50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ser Gly Ser Ile Glu Gly Arg Leu Arg Lys Gln
225                 230                 235                 240

Gly Ser Gly Ser Lys Gly Glu Glu Leu Phe Thr Gly Val Val Pro Ile
                245                 250                 255

Leu Val Glu Leu Asp Gly Asp Val Asn Gly His Lys Phe Ser Val Ser
            260                 265                 270

Gly Glu Gly Glu Gly Asp Ala Thr Tyr Gly Lys Leu Thr Leu Lys Phe
        275                 280                 285
```

```
Ile Cys Thr Thr Gly Lys Leu Pro Val Pro Trp Pro Thr Leu Val Thr
290                 295                 300

Thr Leu Thr His Gly Val Gln Cys Phe Ser Arg Tyr Pro Asp His Met
305                 310                 315                 320

Lys Gln His Asp Phe Phe Lys Ser Ala Met Pro Glu Gly Tyr Val Gln
                325                 330                 335

Glu Arg Thr Ile Phe Phe Lys Asp Asp Gly Asn Tyr Lys Thr Arg Ala
                340                 345                 350

Glu Val Lys Phe Glu Gly Asp Thr Leu Val Asn Arg Ile Glu Leu Lys
                355                 360                 365

Gly Ile Asp Phe Lys Glu Asp Gly Asn Ile Leu Gly His Lys Leu Glu
370                 375                 380

Tyr Asn Phe Asn Ser His Asn Val Tyr Ile Met Ala Asp Lys Gln Lys
385                 390                 395                 400

Asn Gly Ile Lys Val Asn Phe Lys Ile Arg His Asn Ile Glu Asp Gly
                405                 410                 415

Ser Val Gln Leu Ala Asp His Tyr Gln Gln Asn Thr Pro Ile Gly Asp
                420                 425                 430

Gly Pro Val Leu Leu Pro Asp Asn His Tyr Leu Ser Thr Gln Ser Ala
                435                 440                 445

Leu Ser Lys Asp Pro Asn Glu Lys Arg Asp His Met Val Leu Leu Glu
450                 455                 460

Phe Val Thr Ala Ala Gly Ile Thr Leu Gly Met Asp Glu Leu Tyr Lys
465                 470                 475                 480

Glx
```

<210> SEQ ID NO 39
<211> LENGTH: 608
<212> TYPE: PRT
<213> ORGANISM: Artificial sequence
<220> FEATURE:
<223> OTHER INFORMATION: synthetic construct

<400> SEQUENCE: 39

```
Gly Ser Ala Thr Ala Ala Thr Val Pro Pro Ala Pro Ala Gly Glu
1               5                   10                  15

Gly Gly Pro Pro Ala Pro Pro Pro Asn Leu Thr Ser Asn Arg Arg Leu
                20                  25                  30

Gln Gln Thr Gln Ala Gln Val Asp Glu Val Val Asp Ile Met Arg Val
            35                  40                  45

Asn Val Asp Lys Val Leu Glu Arg Asp Gln Lys Leu Ser Glu Leu Asp
50                  55                  60

Asp Arg Ala Asp Ala Leu Gln Ala Gly Ala Ser Gln Phe Glu Thr Ser
65                  70                  75                  80

Ala Ala Lys Leu Lys Arg Lys Tyr Trp Trp Lys Asn Leu Lys Met Met
                85                  90                  95

Ile Ile Leu Gly Val Ile Cys Ala Ile Ile Leu Ile Ile Ile Ile Val
                100                 105                 110

Tyr Phe Ser Thr Gly Ser Gly Ser Gly Ser Gly Ser Gly Ser Gly Pro
                115                 120                 125

Val Ser Lys Gly Glu Glu Leu Phe Thr Gly Val Val Pro Ile Leu Val
                130                 135                 140

Glu Leu Asp Gly Asp Val Asn Gly His Lys Phe Ser Val Ser Gly Glu
145                 150                 155                 160

Gly Glu Gly Asp Ala Thr Tyr Gly Lys Leu Thr Leu Lys Phe Ile Cys
```

```
                    165                 170                 175
Thr Thr Gly Lys Leu Pro Val Pro Trp Pro Thr Leu Val Thr Thr Leu
            180                 185                 190
Thr His Gly Val Gln Cys Phe Ser Arg Tyr Pro Asp His Met Lys Gln
            195                 200                 205
His Asp Phe Phe Lys Ser Ala Met Pro Glu Gly Tyr Val Gln Glu Arg
            210                 215                 220
Thr Ile Phe Phe Lys Asp Asp Gly Asn Tyr Lys Thr Arg Ala Glu Val
225                 230                 235                 240
Lys Phe Glu Gly Asp Thr Leu Val Asn Arg Ile Glu Leu Lys Gly Ile
                245                 250                 255
Asp Phe Lys Glu Asp Gly Asn Ile Leu Gly His Lys Leu Glu Tyr Asn
                260                 265                 270
Phe Asn Ser His Asn Val Tyr Ile Met Ala Asp Lys Gln Lys Asn Gly
                275                 280                 285
Ile Lys Val Asn Phe Lys Ile Arg His Asn Ile Glu Asp Gly Ser Val
                290                 295                 300
Gln Leu Ala Asp His Tyr Gln Gln Asn Thr Pro Ile Gly Asp Gly Pro
305                 310                 315                 320
Val Leu Leu Pro Asp Asn His Tyr Leu Ser Thr Gln Ser Ala Leu Ser
                325                 330                 335
Lys Asp Pro Asn Glu Lys Arg Asp His Met Val Leu Leu Glu Phe Val
                340                 345                 350
Thr Ala Ala Gly Ser Gly Ser Ile Glu Gly Arg Arg Lys Leu Gln Gly
                355                 360                 365
Ser Gly Ser Lys Gly Glu Glu Leu Phe Thr Gly Val Val Pro Ile Leu
        370                 375                 380
Val Glu Leu Asp Gly Asp Val Asn Gly His Lys Phe Ser Val Ser Gly
385                 390                 395                 400
Glu Gly Glu Gly Asp Ala Thr Tyr Gly Lys Leu Thr Leu Lys Ile Phe
                405                 410                 415
Cys Thr Thr Gly Lys Leu Pro Val Pro Trp Pro Thr Leu Val Thr Thr
                420                 425                 430
Leu Thr Tyr Gly Val Gln Cys Phe Ser Arg Tyr Pro Asp His Met Lys
            435                 440                 445
Gln His Asp Phe Phe Lys Ser Ala Met Pro Glu Gly Tyr Val Gln Glu
        450                 455                 460
Arg Thr Ile Phe Phe Lys Asp Asp Gly Asn Tyr Lys Thr Arg Ala Glu
465                 470                 475                 480
Val Lys Phe Glu Gly Asp Thr Leu Val Asn Arg Ile Glu Leu Lys Gly
                485                 490                 495
Ile Asp Phe Lys Glu Asp Gly Asn Ile Leu Gly His Lys Leu Glu Tyr
                500                 505                 510
Asn Tyr Asn Ser His Asn Val Tyr Ile Met Ala Asp Lys Gln Lys Asn
            515                 520                 525
Gly Ile Lys Val Asn Phe Lys Ile Arg His Asn Ile Glu Asp Gly Ser
            530                 535                 540
Val Gln Leu Ala Asp His Tyr Gln Gln Asn Thr Pro Ile Gly Asp Gly
545                 550                 555                 560
Pro Val Leu Leu Pro Asp Asn His Tyr Leu Ser Thr Gln Ser Ala Leu
                565                 570                 575
```

```
Ser Lys Asp Pro Asn Glu Lys Arg Asp His Met Val Leu Leu Glu Phe
            580                 585                 590

Val Thr Ala Ala Gly Ile Thr Leu Gly Met Asp Glu Leu Tyr Lys Glx
            595                 600                 605
```

MULTIPARAMETER FACS ASSAYS TO DETECT ALTERATIONS IN EXOCYTOSIS

FIELD OF THE INVENTION

The invention relates to novel methods of detecting alterations in exocytosis in a cell or a cell population and screening for agents capable of modulating exocytosis through the use of multiparameter assays and a fluorescence-activated cell sorter (FACS) machine.

BACKGROUND OF THE INVENTION

Exocytosis is the fusion of secretory vesicles with the cellular plasma membrane, and has two main functions. One is the discharge of the vesicle contents into the extracellular space, and the second is the incorporation of new proteins and lipids into the plasma membrane itself.

Exocytosis can be divided into two classes: constitutive and regulated. All eukaryotic cells exhibit constitutive exocytosis, which is marked by the continuous fusion of the secretory vesicles after formation. Regulated exocytosis is restricted to certain cells, including exocrine, endocrine and neuronal cells. Regulated exocytosis results in the accumulation of the secretory vesicles that fuse with the plasma membrane only upon receipt of an appropriate signal, usually (but not always) an increase in the cytosolic free $Ca^{2+}$ concentration.

Regulated exocytosis is crucial to many specialized cells, and often a particular cell can release multiple mediators from the same exocytic granules which work in concert to produce a coordinated physiological response in the target cells. These regulated exocytic cells include neurons (neurotransmitter release), adrenal chromaffin cells (adrenaline secretion), pancreatic acinar cells (digestive enzyme secretion), pancreatic β-cells (insulin secretion), mast cells (histamine secretion), mammary cells (milk protein secretion), sperm (enzyme secretion), egg cells (creation of fertilization envelope) and adipocytes (insertion of glucose transporters into the plasma membrane). In addition, current theory suggests that the basic mechanisms of vesicle docking and fusion is conserved from yeast to the mammalian brain.

In addition, disorders involving exocytosis are known. For example, inflammatory mediator release from mast cells leads to a variety of disorders, including asthma. In the United States alone, over 50 million people suffer from asthma, rhinitis, or some other form of allergy. Therapy for allergy remains limited to blocking the mediators released by mast cells (anti-histamines), non-specific anti-inflammatory agents such as steroids and mast cell stabilizers which are only marginally effective at limiting the symtomatology of allergy. Similarly, Chediak-Higashi Syndrome (CHS) is a rare autosomal recessive disease in which neutrophils, monocytes and lymphocytes and most cells contain giant cytoplasmic granules. Similar disorders have been described in mice, mink, cattle, cats and killer whales, with the murine homolog of CHS (designated beige or bg) being the best characterized. See Perou et al., J. Biol. Chem. 272(47):29790 (1997) and Barbosa et al., Nature 382:262 (1996), both of which are hereby incorporated by reference.

Furthermore, it is widely believed that a wide array of psychiatric disorders are the result of an imbalance between neurotransmitter exocytosis and mediator reuptake.

A large number of pharmaceuticals have been designed to specifically interfere with the exocytic mediators primarily through blockade of their receptors. However, this approach is limited by the fact that a single receptor blocker cannot overcome the effects of many diverse mediators.

Accordingly, it is an object of the present invention to provide methods for screening for alterations in exocytosis, particularly for screening for agents capable of mediating such exocytosis. It is also an object to provide such screening methods wherein assay background is reduced and specificity is increased.

SUMMARY OF THE INVENTION

In accordance with the objects outlined above, the present invention provides a method for screening for alterations in exocytosis of a population of cells or in single cells under different conditions or combined with different bioactive agents. The methods comprise sorting the cells in a FACS machine by assaying for alterations in at least three of the properties selected from the group consisting of light scattering, fluorescent dye uptake, fluorescent dye release, annexin granule binding, surface granule enzyme activity, and the quantity of granule specific proteins.

Also provided herein is a method for screening for a bioactive agent capable of modulating exocytosis in a cell. This method comprises combining a candidate bioactive agent and a population of cells and subjecting said cells to conditions that normally cause exocytosis. The cells are sorted in a FACS machine by assaying for alterations in at least three of the properties selected from the group consisting of light scattering, fluorescent dye uptake, fluorescent dye release, annexin granule binding, surface granule enzyme activity, and the quantity of granule specific proteins. Alterations in at least one of said properties as compared to cells that were not exposed to the candidate bioactive agent indicates that said agent modulates exocytosis.

In a preferred embodiment of the method for screening for a bioactive agent, the properties selected include at least one property selected from the group consisting of fluorescent dye release, annexin granule binding, surface granule enzyme activity, and the quantity of granule specific proteins.

When fluorescent dye uptake is detected, the dye is preferably a styryl dye. In the case that fluorescent dye release is detected, the dye can be a low pH concentration dye or a styryl dye.

In a preferred embodiment, the surface granule enzyme activity is detected by an in situ enzymology assay or by a population based enzyme assay. The enzyme substrate can be any detectable substrate. Preferably, the enzyme substrate is coupled to a FRET construct. FRET constructs include two fluorescent proteins divided by a protease site. In this case, the protease site is specific for a granule protease.

In a preferred embodiment, granule specific proteins are detected. The granule specific proteins can be any detectable protein. In one embodiment, the granule specific proteins are fusion proteins comprising a granule specific protein and a detectable molecule which can be a FRET construct.

In another preferred embodiment, a method for screening for a bioactive agent capable of modulating exocytosis in a cell is provided wherein said method comprises combining at least one candidate bioactive agent and a population of cells each containing a fusion nucleic acid comprising a nucleic acid encoding a granule-specific protein and a label. The cells are subjected to conditions that normally cause exocytosis and the alterations in the quantity of the label is detected. Alterations in the quantity of the label indicates that the agent modulates exocytosis. Preferably, the label is an epitope tag or a fluorescent molecule. In a preferred embodiment, the fluorescent molecule is a FRET construct.

In another preferred embodiment, a method for screening for a bioactive agent capable of modulating exocytosis in a cell is provided which comprises combining at least one candidate bioactive agent and a population of cells. The cells are subjected to conditions that normally cause exocytosis and a fluorescent annexin is added. Alterations in the amount of the fluorescent annexin on the surface of the cells is evaluated.

In another preferred embodiment, a method for screening for a bioactive agent capable of modulating exocytosis in a cell is provided which comprises providing a population of cells wherein the cells have taken in a low pH concentration dye. The low pH concentration dye loaded cells are combined with at least one candidate bioactive agent and subjected to conditions that normally cause exocytosis. The release of the low pH concentration dye is detected. Alterations in the amount of released dye indicate that the agent modulates exocytosis.

In another preferred embodiment, a method for screening for a bioactive agent capable of modulating exocytosis in a cell is provided which comprises combining at least one candidate bioactive agent and a population of cells. The cells are subjected to conditions that normally cause exocytosis and a fluorescent substrate specific to a granule enzyme is added. The fluorescent substrate specific to a granule enzyme is detected, wherein alterations in the amount of the fluorescent substrate indicate that the agent modulates exocytosis. In a preferred embodiment, the substrate comprises a FRET construct.

BRIEF DESCRIPTION OF THE DRAWINGS

FIGS. 1A and 1B depict bar graphs showing the results of a population based exocytic enzyme activity assay for exocytosis. FIG. 1A shows glucuronidase or hexosaminidase activity in the supernatant of cells combined with DMSO (−) or ionomycin (+). FIG. 1B shows hexosaminidase activity in the supernatant of cells sensitized with varying amounts of IgE anti-DNP and stimulated with increasing amounts of the antigen BSA-DNP.

FIGS. 2A–2F show exocytic light scatter changes observed on the flow cytometer, side scatter vs. forward scatter, plotted as bivariate histograms for RBL-2H3 cells (FIGS. 2A and 2D) and MC-9 cells (FIGS. 2B, 2C, 2E and 2F). After stimulation with an ionophore, the cells were observed at 0 minutes (FIGS. 2A and 2C), 5 minutes (FIG. 2E), 10 minutes (FIG. 2D), and 30 minutes (FIGS. 2B and 2F).

FIGS. 3A–3E show graphs of the results of a styryl dye assay to detect exocytosis by FACS. Cells were combined with (blue) DMSO or (red) ionomycin in the presence of either FM 4-64 (FIGS. 3A and 3B) or FM 1-43 (FIGS. 3C, 3D and 3E). FIGS. 3A and 3C show cells detected in fluorescence channel 1. FIGS. 3B and 3D show cells detected in fluorescence channel 3. FIG. 3E shows the mean channel shift detected in the flow cytometer in fluorescence channel 1 plotted as a bar graph wherein cells were preincubated with varying doses of the PI-3 kinase inhibitor wortmannin prior to administration of an ionophore (bars 1–4) or DMSO (bar 5) in the presence of FM 1-43.

FIGS. 4A–4D show graphs depicting the results of an annexin-V detection assay of exocytosis by FACS. Cells were combined with either DMSO (FIGS. 4A and 4B) or ionomycin (FIGS. 4C and 4D) and then stained with both propidium iodide (FIGS. 4A and 4C) and annexin-V-FITC (FIGS. 4B and 4D).

FIGS. 5A–5D show the results of an annexin-V-FITC detection assay of exocytosis visualized by confocal microscopy. Cells were combined with ionomycin (FIGS. 5A, 5B and 5C) or DMSO (FIG. 5D), stained with annexin-V-FITC and mounted for confocal microscopy.

FIGS. 6A and 6B show annexin-V-FITC staining of exocytic granules in cells stimulated with antigen crosslinking. Cells were sensitized with IgE and combined with either buffer only (FIG. 6A) or BSA-DNP antigen (FIG. 6B) and then stained with annexin-V-FITC.

FIGS. 7A–7C show graphs indicating the results of an in situ enzymology assay of exocytosing cells visualized by FACS. Cells were combined with DMSO (FIG. 7A) or an ionophore (FIGS. 7B and 7C) and then stained for in situ glucuronidase activity. FIG. 7C shows the pH profile of the cell surface enzymatic activity wherein the bar graphs represent the percentage of maximal signal, as measured by mean channel shift in the flow cytometer, observed.

FIG. 8 is a histogram of fluorescence intensity detected in channel 1 showing cells loaded with LYSOTRACKER GREEN™, combined with either DMSO (blue line) or ionomycin (red line (left)) and viewed in the flow cytometer.

FIGS. 9A–9H show the results of a multiparameter analysis including detection of LYSOTRACKER GREEN™, annexin-V-APC and forward and side scatter. FIGS. 9A–9D and 9E–9H each show cells treated with increasing doses of ionomycin and observed in the flow cytometer with four parameters simultaneously. The cells were loaded with low pH concentration dye, stimulated and stained with annexin-V-APC. FIGS. 9A–9D show bivariate histograms of side vs. forward light scatter and FIGS. 9E–9H show bivariate histograms of annexin-V-APC vs. low pH concentration dye signals.

FIGS. 10A–10D show the results of another multiparameter analysis for exocytosis using FM 1-43, annexin-V-APC, forward and side scatter. Cells were treated with either DMSO (FIGS. 10A and 10B) or ionomycin (FIGS. 10C and 10D) and observed in the flow cytometer with four parameters simultaneously. The cells were stimulated in the presence of FM 1-43 and stained for annexin-V-APC. FIGS. 10A and 10C show bivariate histograms of side vs. forward light scatter. FIGS. 10B and 10D show bivariate histograms of Annexin-V-APC vs. FM 1-43.

FIG. 11 shows a graph of cells stimulated in the presence of FM 1-43 and annexin-V-APC stained. At various timepoints after ionomycin stimulation the cells were analyzed by flow cytometry and the supernatant for enzymatic activity (cell supernatant). The parameters forward scatter, FM-143, annexin-V-APC, and hexosaminidase are plotted on the graph relative to the maximal response for each parameter. For calcium signaling, a separate tube of cells was loaded with Fluo-3 and underwent the identical procedure.

DETAILED DESCRIPTION OF THE INVENTION

The present invention is directed to the detection of alterations in exocytosis, generally through the use of a fluorescence-activated cell sorter (FACS) machine. There are a number of parameters that may be evaluated or assayed to allow the detection of alterations in exocytotic pathways, including, but not limited to, light scattering, fluorescent dye uptake, fluorescent dye release, granule exposure, surface granule enzyme activity, and the quantity of granule specific proteins. By assaying or measuring one or more of these parameters, it is possible to detect not only alterations in exocytosis, but alterations of different steps of the exocytotic pathway. In addition, multiparameter analysis also reduces the background, or "false positives", that are detected. In this manner, rapid, accurate screening of candidate agents may be performed to identify agents that modulate exocytosis.

In a preferred embodiment, the invention provides methods for screening for alterations in exocytosis of a population of cells. By "alteration" or "modulation" (used herein interchangeably), is meant a decrease or an increase in the amount of exocytosis in one cell compared to another cell or in the same cell under different conditions. The measurements can be determined wherein all of the conditions are the same for each measurement, or under various conditions, with or without bioactive agents, or at different stages of the exocytic process. For example, a measurement of exocytosis can be determined in a cell population wherein a candidate bioactive agent is present and wherein the candidate bioactive agent is absent. In another example, the measurements of exocytosis are determined wherein the condition or environment of the populations of cells differ from one another. For example, the cells may be evaluated in the presence or absence of physiological signals, such as exocytic inducers (i.e, $Ca^{++}$, ionomycin, etc.), hormones, antibodies, peptides, antigens, cytokines, growth factors, action potentials, or other cells (i.e. cell—cell contacts). In another example, the measurements of exocytosis are determined at different stages of the exocytic process. In yet another example, the measurements of exocytosis are taken wherein the conditions are the same, and the alterations are between one cell or cell population and another cell or cell population.

By a "population of cells" herein is meant a sample of cells. The sample can contain a mixture of different cell types from either primary or secondary cultures although samples containing only a single cell type are preferred, for example, the sample can be from a cell line. In a preferred embodiment, the population of cells contains at least one cell type containing secretory vesicles. Preferably, although not required, the cells are rapidly growing, retrovirally injectable, and are compatible with dyes and antibodies. Preferred cell types for use in the invention include, but are not limited to, mast cells, neurons, adrenal chromaffin cells, basophils, endocrine cells including pancreatic β-cells, pancreatic acinar cells including exocrine cells, neutrophils, monocytes, lymphocytes, mammary cells, sperm, egg cells and PMN leukocytes, endothelial cells, adipocytes, and muscle cells.

The methods comprise sorting the cells in a FACS machine by assaying for alterations in at least three of the properties selected from the group consisting of light scattering, fluorescent dye uptake, fluorescent dye release, granule exposure, surface granule enzyme activity, and the quantity of granule specific proteins. In a preferred embodiment, each of the measurements is determined simultaneously from an individual cell as it passes through the beam paths of multiple lasers. Alternatively, the measurements are done sequentially. By using more than one parameter to detect exocytosis or alterations in exocytosis, background is reduced and specificity is increased. The cells meeting the parameters of the desired properties can be physically sorted from cells not meeting the desired parameters or they can be identified by their percentage in the cell population.

In a preferred embodiment, changes in light scattering are assayed to determine alterations in exocytosis in a population of cells. When viewed in the FACS, cells have particular characteristics as measured by their forward and 90 degree (side) light scatter properties. These scatter properties represent the size, shape and granule content of the cells. Upon activation of the cells with a pro-exocytic stimulus, both the forward and side scatter properties of the cells changes considerably. These properties account for two parameters to be measured as a readout for the exocytic event. These properties change in proportion to the extent of exocytosis of the cells and depend on the time course of the exocytic events as well. Alterations in the intensity of light scattering, or the cell-refractive index indicate alterations in exocytosis either in the same cell at different times, or compared to the same cell under different conditions or with candidate bioactive agents present or absent, or compared to different cells or cell populations.

In one embodiment provided herein, a cell population is combined with an agent which is known to stimulate exocytosis and the light scattering properties are determined. Cells having light scattering properties indicating the desirable exocytic activity can be identified and/or sorted. Exocytic activity as used herein includes lack of activity. In a preferred embodiment, candidate bioactive agents are combined with the cell population prior to or with the exocytic stimulus, as is more fully outlined below. In this embodiment, where light scattering properties differ as between a) a cell population combined with a known exocytic stimulus and a candidate bioactive agent, and b) a cell population combined with a known exocytic stimulus wherein the candidate bioactive agent is absent, it can be determined that the candidate bioactive agent modulates exocytosis. It may also be desirable in some cases to include an inhibitor of exocytosis or to exclude the exocytic stimulus to identify bioactive agents which induce exocytosis. Preferably, light scattering properties are measured in combination with at least one, and preferably two other properties which indicate exocytosis activity. General methodologies for light scattering measurements are further described in Perretti, et al., J. Pharmacol. Methods, 23(3):187–194 (1990) and Hide et al., J. Cell Biol., 123(3):585–593 (1993), both incorporated herein by reference. In general, changes of at least about 5% from baseline are preferred, with at least about 25% being more preferred, at least about 50% being particularly preferred, and at least about 75 to 100% being especially preferred. Baseline in this case generally means the light scatter properties of the cells prior to exocytotic stimulation. In each case provided herein, the baseline may also be set for any control parameter. For example, the baseline may be set at the exocytosis measurement of a particular cell, a similar cell under different conditions, or at a particular time point during exocytosis.

In another preferred embodiment, changes in fluorescent dye uptake are evaluated. Preferred fluorescent dyes include styryl dyes, which indicate exocytosis activity in relation to endocytosis, sometimes referred to as coupled endocytosis. The theory behind coupled endocytosis is that cells undergoing exocytosis must also undergo endocytosis in order to maintain cell volume and membrane integrity. Thus, upon exocytic stimulation, endocytosis is also increased, providing an indirect measurement of exocytosis by quantifying the amount of styryl dye uptake.

In an embodiment provided herein, the cells are bathed in a solution of styryl dye and stimulated with a pro-exocytic stimulus and the dye is quantitated. Preferably, after exocytic stimulation, the cells are spun down, aspirated and resuspended in fresh buffer. In a preferred embodiment, a candidate bioactive agent is combined with the cells as described herein. In some cases, the candidate bioactive agent can be combined with the cells with an inhibitor of exocytosis or without the pro-exocytic stimulus. Preferably, a pro-exocytic stimulus is added to the cell population which results in a dramatic increase in the fluorescence signal of the dye. The increased cell associated signal is due to coupled endocytosis of the styryl dye and is proportional to the exocytic response in both time and intensity. Conversely, the signal is not increased wherein exocytosis is inhibited or is not induced. Alterations are determined by measuring the fluorescence at either different time points or in different cell populations, and comparing the determinations to one another or to standards. In general, changes of at least about 50% from baseline are preferred, with changes of at least about 75%–100% being more preferred, changes of at least about 250% being particularly preferred, and changes of at least about 1000–2000% being especially preferred. Baseline in this case means the styryl dye uptake of cells prior to exocytic stimulation.

Preferred styryl dyes include, but are not limited to FM1-43, FM4-64, FM 14-68, FM2-10, FM4-84, FM1-84, FM14-27, FM14-29, FM3-25, FM3-14, FM5-55, RH414, FM6-55, FM10-75, FM1-81, FM9-49, FM4-95, FM4-59, FM9-40, and combinations thereof. Preferred dyes such as FM 1-43 are only weakly fluorescent in water but very fluorescent when associated with a membrane, such that dye uptake is readily discernable. Suitable dyes are available commercially, i.e., Molecular Probes, Inc., of Eugene, Oreg., "Handbook of Fluorescent Probes and Research Chemicals", 6th Edition, 1996, particularly, Chapter 17, and more particularly, Section 2 of Chapter 17, (including referenced related chapter), hereby incorporated herein by reference. Preferably, the dyes are provided in a solution wherein the dye concentration is about 25 to 1000–5000 nM, with from about 50 to about 1000 nM being preferred, and from about 50 to 250 being particularly preferred. The use of styryl dyes is further described in Betz, et al., Current Opinion in Neurobiology, 6:365–371 (1996) also incorporated herein by reference. Preferably, fluorescent dye uptake is measured in combination with at least one, and preferably two other indicators of exocytosis activity.

In another preferred embodiment, changes in fluorescent dye release are evaluated. The present invention is in part directed to the discovery that low pH concentration dyes, which are normally used to stain lysozomes, also low pH stain exocytic granules. Generally, these dyes can be taken up by the cells passively and concentrate in granules; however, the cells can be induced to take up the dye, i.e., by coupled endocytosis. In a preferred embodiment, a cell population is bathed in a low pH concentration dye such that the dye is taken up by the cells. The cells are preferably washed. The cells can be exposed to a pro-exocytic stimulus and/or inhibitor. In a preferred embodiment, a candidate bioactive agent is combined with the cell population and preferably, the pro-exocytic stimulus. Fluorescence is evaluated. Changes in fluorescent dye release between cells or at different time points in the same cell indicate alterations in exocytosis. Preferably, the alterations are between cells, and most preferably, between cells having different bioactive agents added thereto. Changes of at least about 5% from baseline are preferred, with at least about 25% being more preferred, at least about 50% being particularly preferred and at least about 100% being especially preferred. Baseline in this case means the amount of dye in the cells prior to stimulation.

In this embodiment, low pH concentration dyes are preferred. Such low pH concentration dyes include but are not limited to acridine orange, LYSOTRACKER™ red, LYSOTRACKER™ green, and LYSOTRACKER™ blue. Such dyes are commercially available, i.e., from Molecular Probes, supra, particularly including Chapter 17, Section 4 of Chapter 17, and referenced "related chapters", i.e., Chapter 23. In preferred embodiments, the dyes are administered in a solution wherein the dye is a concentration of about 50 nM to about 25 $\mu$M, with from about 5 $\mu$M to about 25 $\mu$M being preferred, and from about 1 to 5 $\mu$M being particularly preferred. The use of low pH concentration dyes is generally described (in regards to lysozome studies) in Haller; et al., Cell Calcium, 19(2):157–165 (1996), hereby incorporated herein by reference.

In an alternative embodiment wherein changes in fluorescent dye release are evaluated, the fluorescence released into the supernatant is evaluated. In this embodiment, either styryl dyes, which reversibly label endocytosed membranes, or low pH concentration dyes are used. In this embodiment, a cell population is bathed in dye such that the dye is taken up into the cells passively or by induction. The cells are then preferably washed. The cells can be exposed to a pro-exocytic stimulus and/or inhibitor, and optionally, a candidate bioactive agent. The cells which are exposed to a pro-exocytic stimulus will release the dye into the extracellular medium. The fluorescence in the medium can be measured or detected. This process is sometimes referred to as destaining the cells. Optionally, an agent for improving and facilitating the detection of the dye in the medium can be added. For example, micelle-forming detergents such as 3-[(3-cholamidopropyl)dimethylammonio]-1-propanesulfonate (CHAPS) increase the fluorescence and thereby allow detection of small amounts of exocytosis activity. Changes in the release of dye will indicate alterations in exocytosis in the same cell, between cells, and most preferably, between cells having different bioactive agents added thereto. In general, changes of at least about 5% from baseline are preferred, with at least about 25% being more preferred, with at least about 50% being particularly preferred and at least about 100% being especially preferred. Baseline in this case means the release of dye prior to exocytotic stimulus. Preferably, dye release when measured in the media is combined with the evaluation of at least one other exocytosis indicator.

In a preferred embodiment, changes in granule exposure are determined. The granules are exposed to the media during exocytosis, i.e., the granules fuse with the cell membrane and expose/release their contents. Therefore, granule exposure is indicative of exocytic activity, and its absence is indicative that exocytosis has not been induced, or has been inhibited. Preferably, granule exposure is detected by a detectable agent which specifically bind to granules. An example of a detectable agent used herein is annexin V, a member of a protein family which displays specific binding to phospholipid (phosphotidylserine) in a divalent ion dependent manner. This protein has been widely used for the measurement of apoptosis (programmed cell death) as cell surface exposure of phosphatidylserine is a hallmark early signal of this process. Surprisingly, it has been determined herein that annexin V specifically binds to exocytic granules when they are exposed at the cell surface during the secretory process; granules internal to the cell are unlabeled. This property of annexin V is used herein to create a single exocytosis assay based on its exocytosis dependent binding. Upon exocytic stimulation of cells, the cells show an increase in annexin binding and fluorescent signal in proportion in both time and intensity to the exocytic response. In this embodiment, annexin is labelled, either directly or indirectly, and combined with a cell population.

Annexin is commercially available, i.e., from PharMingen, San Diego, Calif., or Caltag Laboratories, Millbrae, Calif. Preferably, the annexin is provided in a solution wherein the annexin is in a concentration of about 100 ng/ml to about 500 ng/ml, more preferably, about 500 ng/ml to about 1 µg/ml, and most preferably, from about 1 µg/ml to about 5 µg/ml. In a preferred embodiment, the annexin is directly labelled; for example, annexin may be labelled with a fluorochrome such as fluorescein isothiocyanate (FITC), Alexa dyes, TRITC, AMCA, APC, tricolor, Cy-5, and others known in the art or commercially available. In an alternate preferred embodiment, the annexin is labelled with a first label, such as a hapten such as biotin, and a secondary fluorescent label is used, such as fluorescent streptavidin. Other first and second labelling pairs can be used as will be appreciated by those in the art.

In the preferred embodiment, the cells are subjected to conditions that normally cause exocytosis. Optionally, a candidate bioactive agent is added to the cells. In some cases, it may be desirable to include an inhibitor of exocytosis to determine whether the candidate agent can reverse the inhibition, or to add the candidate bioactive agent without an exocytotic stimulus to determine whether the agent induces exocytosis. The cells are preferably washed and fluorescence is detected in the microscope or on the flow cytometer. Alterations in the detection of annexin binding indicates alterations in exocytosis in the same cell, or between different cells, with or with the same conditions and/or agents combined therewith. In general, changes of at least about 25% from baseline are preferred, with at least about 50% being more preferred, at least about 100% being particularly preferred and at least about 500% being especially preferred. Baseline in this case means the amount of annexin binding prior to exocytotic stimulation.

In another preferred embodiment, granule exposure is detected by a cationic dye such as berberine or ruthenium red. Such cationic dyes specifically stain secreting granules. Thus, when exocytosis occurs, and secreting granules are exposed at the cell surface, an increase in fluorescence can be detected. In a preferred embodiment, the cationic dye is combined with a cell population in the presence or absence of an exocytic stimulus and/or inhibitor, and optionally, in the presence or absence of a candidate bioactive agent. In a particularly preferred embodiment, the berberine is combined with a cell and an exocytic stimulus and a candidate bioactive agent to determine whether the candidate bioactive agent can modulate the exocytic activity. Preferably, the cells are washed and then fluorescence is determined. In preferred embodiments, cationic dye evaluation is combined with evaluation of at least one other indicator of exocytosis. The dye is combined with the cells as is known in the art. General methodologies describing berberine are described in Berlin and Enerback, Int. Arch. Allergy Appl. Immunol., 73(3):256–262 (1984) hereby incorporated by reference. In general, changes of at least about 5% from baseline are preferred, with at least about 25% being more preferred, at least about 50% being particularly preferred, and at least about 100% being especially preferred. Baseline in this case means the amount of dye binding prior to stimulation.

Similarly, Con A-FITC can be used, as it binds to the carbohydrate on granule proteins, in a manner similar to those outlined herein.

In another preferred embodiment, changes in surface granule enzyme activity is determined. Secretory granules contain enzymes such as proteases and glycosidases which are released as part of the exocytic process. Frequently, these enzymes are inactive within the granule, due to the low pH, but upon exposure to the extracellular media at physiological pH, they become activated. These enzyme activities can be measured using chromogenic or fluorogenic substrates as components of the extracellular media. This allows detection of exocytic cells in varying approaches.

In one embodiment, sometimes called herein the population based enzyme assay, the generation of signal via cleavage of a chromogenic or fluorogenic substrate can be quantified in the media. That is, the amount of detectable reaction product in the media is related to the amount of enzyme present, and thus to the amount of exocytosis. In this embodiment, it is the media, not the cells, that becomes detectable.

In a preferred embodiment, cells are subjected to an exocytic stimulus, and optionally, a candidate bioactive agent. The chromogenic or fluorogenic substrate is added to the media, and changes in the signal are evaluated, as the enzymes cleave the extracellular substrates.

In an alternate preferred embodiment, sometimes called herein "in situ enzymology assay", fluorogenic substrates that precipitate upon cleavage are used. That is, upon exocytosis a considerable amount of enzyme activity remains cell/granule associated and can be visualized using fluorescent substrates which precipitate at the site of activity. For example, substrates for glucuronidase, such as ELF-97 glucuronide, precipitate on exocytosing cells, but not resting cells, and thus the cells can show increased fluorescence. The fluorescence is a direct measurement of exocytosis and is pH dependent reflecting the pH optima of the exocytosed enzyme. This method also provides a method of distinguishing different subtypes of granules based on their enzyme profile.

In a preferred embodiment, the cell population is subjected to an exocytotic stimulus and then incubated with a detectable substrate. A candidate bioactive agent is optionally added. The cells are washed and then viewed in the microscope or flow cytometer.

Preferred granule enzymes include but are not limited to chymase, tryptase, arylsulfatase A, beta-hexosaminidase, beta-glucuronidase, and beta-D-galactosidase. Substrates include ELF-97 glucuronide, N-acetyl beta-D glucoronide, ELF-97 coupled to peptides, etc., many of which are commercially available, i.e., from Molecular Probes, supra, particular Chapter 10, more particularly Section 2 of Chapter 10, and referenced "related chapters".

By detectable substrate is meant that the substrate comprises a fluorescent molecule as further described herein, or can be detected with a fluorescent molecule specific for the substrate or cleaved substrate, i.e., a fluorescent antibody. In a preferred embodiment, the substrate comprises a detectable molecule formed of two fluorescent proteins, i.e., blue and green fluorescent protein (BFP and GFP), and other similar molecules. As is known in the art, constructs of GFP and BFP that hold these two proteins in close proximity allow fluorescence resonance energy transfer (FRET). That is, the excitation spectra of the GFP overlaps the emission spectra of the BFP. Accordingly, exciting the BFP results in GFP emission. If a protease cleavage site is engineered between the GFP and BFP to form a "FRET construct", upon exposure of the FRET construct to an active protease which cleaves the construct, the GFP and BFP molecules separate. Thus, exciting the BFP results in BFP emission and loss of GFP emission.

Preferably, the protease dependent cleavage site inserted between two fluorescent proteins of the FRET construct is specific for a granule specific enzyme. Thus, the FRET construct can be used for detecting granule specific proteases specific for the cleavage site of the FRET construct. In this embodiment, the protease substrate that is combined with the cells or media includes the FRET construct. The FRET system allows for detection of the detectable molecule in its cleaved and uncleaved state, and distinguishes between the two. The system is further described in Xu et al., Nucleic Acid Res. 26(8):2034 (1998); and Miyawaki et al., Nature 388(6645):882–887 (1997), both of which are incorporated by reference.

The amount of substrate added to the cells or media will depend in part on the enzyme's specific activity and the substrate itself, but generally is about 250 nM to about 1 mM, from about 1 µM to about 100 µM being preferred, and from about 1 µM to about 10 µM being particularly preferred. In general, changes of at least about 5% from baseline are preferred, with at least about 25% being preferred, at least about 100% being particularly preferred and at least about 1000% being especially preferred. Baseline in this case means the amount of substrate cleavage prior to induction of exocytosis.

In a preferred embodiment, changes in the quantity of granule specific proteins are determined. Secretory granules contain proteins which are specifically targeted to the granule compartment due to specific properties of these proteins. Upon exocytic induction, the granule specific proteins are exposed to the surface and detected.

In a preferred embodiment, detectable granule specific proteins are combined with a population of cells and subjected to conditions known to induce exocytosis. Optionally, a bioactive candidate is combined with the cell population and detectable granule specific protein and the granule specific protein is detected. Granule specific proteins include but are not limited to VAMP and synaptotagmin. Also included within the definition of granule specific proteins are the mediators released during exocytosis, including, but not limited to, serotonin, histamine, heparin, hormones, etc.

The quantification of the granule proteins may be done in several ways. In one embodiment, labelled antibodies, (such as fluoroscent antibodies), to granule specific proteins are used. In another embodiment, the cells are engineered to contain fusion proteins comprising a granule protein and a detectable molecule. In a preferred embodiment, a detectable molecule is added to the cells for detection. For example, either directly or indirectly labelled antibodies can be used. A preferred embodiment uses a first labelled antibody, with fluorescent labels preferred. Another embodiment uses a first and second label, for example, a labelled secondary antibody. Generally, this embodiment may use any agent that will specifically bind to the granule protein or compound that can be either directly or indirectly labelled.

In a preferred embodiment the labels are engineered into the cells. For example, recombinant proteins are introduced to the cell population which are fusion proteins of a granule specific protein and a detectable molecule. This is generally done by transforming the cells with a fusion nucleic acid encoding a fusion protein comprising a granule specific protein and a detectable molecule. This is generally done as is known in the art, and will depend on the cell type. Generally, for mammalian cells, retroviral vectors and methods are preferred.

The fusion proteins are constructed by methods known in the art. For example, the nucleic acids encoding the granule specific protein is ligated with a nucleic acid encoding a detectable molecule. By detectable molecule herein is meant a molecule that allows a cell or compound comprising the detectable molecule to be distinguished from one that does not contain it, i.e., an epitope, sometimes called an antigen TAG, or a fluorescent molecule. Preferred fluorescent molecules include but are not limited to GFP, BFP, YFP, enzymes including luciferase and β-galactosidase. These constructs can be made in such a way so that upon exocytosis an epitope, internal to the granule, is exposed at the cell surface and can then be detected. The epitope is preferably any detectable peptide which is not generally found on the cytoplasmic membrane, although in some instances, if the epitope is one normally found on the cells, increases may be detected, although this is generally not preferred.

In a preferred embodiment, the cell population containing the fusion protein or detectable granule specific protein is subjected to exocytic conditions. Optionally, a candidate bioactive agent and/or exocytic inhibitor is included. Preferably, the cells are washed. Fluorescence is detected on the cells. In general, changes of at least about 5% from baseline are preferred, with at least about 25% being more preferred, at least about 50% being particularly preferred and at least about 100% being especially preferred. Generally, baseline in this case means amount of fluorescence prior to exocytic stimulus.

In the invention herein, the same characteristic of exocytosis, is evaluated by multiple parameters which results in reduced background and greater specificity. In contrast, FACS has been used in the past to evaluate two different or unrelated characteristics at the same time which identifies cells having those two characteristics, but does not reduce the background for the combined characteristics. The present invention can, however, in addition to the identification of multiple exocytosis properties, be combined with the identification of other cellular characteristics. For example, parameters of general cellular health can be determined and selected for by using i.e., dye Indo-1 indicating a calcium response or calcein blue indicating viability. Other characteristics which are routinely identified by the skilled artisan include but are not limited to: cell size, cell shape, redox state, DNA content, nucleic acid sequence, chromatin structure, RNA content, total protein, antigens, lipids, surface proteins, intracellular receptors, oxidative metabolism, DNA synthesis and degradation and intracellular pH.

In a preferred embodiment, the cells are subjected to conditions that normally cause exocytosis. Pro-exocytic agents include ionomycin, $Ca^{+31}$, ionophores (Ionomycin, AZ3187), compound 48/80, substance P, complement C3a/C5a, trypsin, tryptase, insulin, interleukin-3, specific IgE, allergen, anti-IgE, or anti-IgG receptor antibodies. These are provided at concentrations depending on the compound as is known in the art, ranging from 1 picomolar to 10 µM, generally. In some cases, it may be desirable to combine the cells with agents which inhibit exocytosis. Exocytosis inhibitors include but are not limited to Wortmannin, and Genestein, and others known in the art.

In a preferred embodiment, the methods are used to screen candidate bioactive agents for the ability to modulate exocytosis. The candidate bioactive agents may be combined with the cell population before, during or after exocytosis is stimulated, preferably before. In some instances, it may be desirable to determine the effect of the candidate bioactive agent, also referred to as "candidate agents" herein, on the cell wherein exocytosis is not induced or wherein exocytosis is inhibited. The candidate bioactive agent can be added to the cell population exogenously or can be introduced into the cells as described further herein.

The term "candidate bioactive agent" or "exogeneous compound" as used herein describes any molecule, e.g., protein, oligopeptide, small organic molecule, polysaccharide, polynucleotide. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

In a preferred embodiment, the candidate bioactive agents are naturally occuring proteins or fragments of naturally occuring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al, Tetrahedron, 49(10):1925 (1993) and references therein; Letsinger, J. Org. Chem., 35:3800 (1970); Sprinzl, et al., Eur. J. Biochem., 81:579 (1977); Letsinger, et al., Nucl. Acids Res. 14:3487 (1986); Sawai, et al., Chem. Lett., 805 (1984), Letsinger, et al., J. Am. Chem. Soc., 110:4470 (1988); and Pauwels, et al, Chemica Scripta, 26:141 (1986)), phosphorothioate (Mag, et al., Nucleic Acids Res., 19:1437 (1991); and U.S. Pat. No. 5,644,048), phosphorodithioate (Briu, et al., J. Am. Chem. Soc., 111:2321 (1989)), O-methylphophoroamidite linkages (see Eckstein, Oligonucleotides and Analogues: A Practical Approach, Oxford University Press), and peptide nucleic acid backbones and linkages (see Egholm, J. Am. Chem. Soc., 114:1895 (1992); Meier, et al., Chem. Int. Ed. Engl., 31:1008 (1992); Nielsen, Nature, 365:566 (1993); Carlsson, et al, Nature, 380:207 (1996), all of which are incorporated by reference)). Other analog nucleic acids include those with positive backbones (Denpcy, et al., Proc. Natl. Acad, Sci. USA, 92:6097 (1995)); non-ionic backbones (U.S. Pat. Nos. 5,386,023; 5,637,684; 5,602,240; 5,216,141; and 4,469,863; Kiedrowshi, et al, Angew. Chem. Intl. Ed. English, 30:423 (1991); Letsinger, et al., J. Am. Chem. Soc., 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., Bioorganic & Medicinal Chem. Lett., 4:395 (1994); Jeffs, et al., J. Biomolecular NMR, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook.

Nucleic acids containing one or more carbocyclic sugars are also included within the definition of nucleic acids (see Jenkins, et al., *Chem. Soc. Rev.*, (1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

As described above generally for proteins, nucleic acid candidate bioactive agents may be naturally occuring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties, a wide variety of which are available in the literature.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

The candidate bioactive agents are combined or added to a cell or population of cells. Suitable cell types for different embodiments are outlined above. By "population of cells" herein is meant at least two cells, with at least about $10^3$ being preferred, at least about $10^6$ being particularly preferred, and at least about $10^8$ being especially preferred.

The candidate bioactive agent and the cells are combined. As will be appreciated by those in the art, this may accomplished in any number of ways, including adding the candidate agents to the surface of the cells, to the media containing the cells, or to a surface on which the cells are growing or in contact with; adding the agents into the cells, for example by using vectors that will introduce the agents into the cells (i.e. when the agents are nucleic acids or proteins).

In a preferred embodiment, the candidate bioactive agents are either nucleic acids or proteins (proteins in this context includes proteins, oligopeptides, and peptides) that are introduced into the host cells using retroviral vectors, as is generally outlined in PCT US97/01019 and PCT US97/01048, both of which are expressly incorporated by reference. Generally, a library of retroviral vectors is made using retroviral packaging cell lines that are helper-defective and are capable of producing all the necessary trans proteins, including gag, pol and env, and RNA molecules that have in cis the Ψ packaging signal. Briefly, the library is generated in a retrovirus DNA construct backbone; standard oligonucleotide synthesis is done to generate either the candidate agent or nucleic acid encoding a protein, for example a random peptide, using techniques well known in the art. After generation of the DNA library, the library is cloned into a first primer. The first primer serves as a "cassette", which is inserted into the retroviral construct. The first primer generally contains a number of elements, including for example, the required regulatory sequences (e.g. translation, transcription, promoters, etc), fusion partners, restriction endonuclease (cloning and subcloning) sites, stop codons (preferably in all three frames), regions of complementarity for second strand priming (preferably at the end of the stop codon region as minor deletions or insertions may occur in the random region), etc.

A second primer is then added, which generally consists of some or all of the complementarity region to prime the first primer and optional necessary sequences for a second unique restriction site for subcloning. DNA polymerase is added to make double-stranded oligonucleotides. The double-stranded oligonucleotides are cleaved with the appropriate subcloning restriction endonucleases and subcloned into the target retroviral vectors, described below.

Any number of suitable retroviral vectors may be used. Generally, the retroviral vectors may include: selectable marker genes under the control of internal ribosome entry sites (IRES), which allows for bicistronic operons and thus greatly facilitates the selection of cells expressing peptides at uniformly high levels; and promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc.

Preferred vectors include a vector based on the murine stem cell virus (MSCV) (see Hawley et al., Gene Therapy 1:136 (1994)) and a modified MFG virus (Rivere et al., Genetics 92:6733 (1995)), and pBABE, outlined in PCT US97/01019.

The retroviruses may include inducible and constitutive promoters for the expression of the candidate agent (to be distinguished from the IL-4 inducible ε promoter). For example, there are situations wherein it is necessary to induce peptide expression only during certain phases of the selection process. A large number of both inducible and constitutive promoters are known.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/ promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

While the candidate bioactive agents may be either nucleic acid or peptides, presentation structures are preferably used with peptide candidate agents. Thus, synthetic presentation structures, i.e. artificial polypeptides, are capable of presenting a randomized peptide as a conformationally-restricted domain. Generally such presentation structures comprise a first portion joined to the N-terminal end of the randomized peptide, and a second portion joined to the C-terminal end of the peptide; that is, the peptide is inserted into the presentation structure, although variations may be made, as outlined below. To increase the functional isolation of the randomized expression product, the presentation structures are selected or designed to have minimal biologically activity when expressed in the target cell.

Preferred presentation structures maximize accessibility to the peptide by presenting it on an exterior loop. Accordingly, suitable presentation structures include, but are not limited to, minibody structures, loops on beta-sheet turns and coiled-coil stem structures in which residues not critical to structure are randomized, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the randomized peptide on an exterior loop. See, for example, Myszka et al., Biochem. 33:2362–2373 (1994), hereby incorporated by reference). Using this system investigators have isolated peptides capable of high affinity interaction with the appropriate target. In general, coiled-coil structures allow for between 6 to 20 randomized positions.

A preferred coiled-coil presentation structure is as follows:

MGC<u>AALESEVSALESEVASLESEVAAL</u>GRGDMP <u>LAAVKSKLSAVKSKLASVKSKLAA</u>CGPP (SEQ ID NO: 1). The underlined regions represent a coiled-coil leucine zipper region defined previously (see Martin et al., EMBO J. 13(22):5303–5309 (1994), incorporated by reference). The bolded GRGDMP region represents the loop structure and when appropriately replaced with randomized peptides (i.e. candidate bioactive agents, generally depicted herein as $(X)_n$, where X is an amino acid residue and n is an integer of at least 5 or 6) can be of variable length. The replacement of the bolded region is facilitated by encoding restriction endonuclease sites in the underlined regions, which allows the direct incorporation of randomized oligonucleotides at these positions. For example, a preferred embodiment generates a XhoI site at the double underlined LE site and a HindIII site at the double-underlined KL site.

In a preferred embodiment, the presentation structure is a minibody structure. A "minibody" is essentially composed of a minimal antibody complementarity region. The minibody presentation structure generally provides two randomizing regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$ for the pro-inflammatory cytokine IL-6.

A preferred minibody presentation structure is as follows: MGRNSQATS*G*FTFSHFYMEWVRGGEYIAASR HKHNKYTTEYSASVKGRYIVSRDTSQ SILYLQKKKGPP (SEQ ID NO:2). The bold, underline regions are the regions which may be randomized. The italicized phenylalanine must be invariant in the first randomizing region. The entire peptide is cloned in a three-oligonucleotide variation of the coiled-coil embodiment, thus allowing two different randomizing regions to be incorporated simultaneously. This embodiment utilizes non-palindromic BstXI sites on the termini.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of random sequences, with or without spacer or linking sequences, may be flanked with cysteine residues. In other embodiments, effective presentation structures may be generated by the random regions themselves. For example, the random regions may be "doped" with cysteine residues which, under the appropriate redox conditions, may result in highly crosslinked structured conformations, similar to a presentation structure. Similarly, the randomization regions may be controlled to contain a certain number of residues to confer β-sheet or α-helical structures.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Thus, suitable targeting sequences include, but are not limited to, binding sequences capable of causing binding of the expression product to a predetermined molecule or class of molecules while retaining bioactivity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLSs such as that of the SV40 (monkey virus) large T Antigen (Pro Lys Lys Lys Arg Lys Val (SEQ ID NO:3), Kalderon (1984), et al., Cell, 39:499–509; the human retinoic acid receptor-β nuclear localization signal (ARRRRP (SEQ ID NO:4)); NF$_\kappa$B p50 (EEVQRKRQKL (SEQ ID NO:5); Ghosh et al., Cell 62:1019 (1990); NF$_\kappa$B p65 (EEKRKRTYE (SEQ ID NO:6); Nolan et al., Cell 64:961 (1991); and others (see for example Boulikas, J. Cell. Biochem. 55(1):32–58 (1994), hereby incorporated by reference) and double basic NLSs exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp (SEQ ID NO:7)), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound peptide libraries are useful for both the identification of important elements in these processes as well as for the discovery of effective inhibitors. The invention provides methods for presenting the randomized expression product extracellularly or in the cytoplasmic space; see FIG. 3. For extracellular presentation, a membrane anchoring region is provided at the carboxyl terminus of the peptide presentation structure. The randomized expression product region is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular randomized expression product region is bound, confers a function on the cells (activation of a kinase, phosphatase, binding of other cellular components to effect function). Similarly, the randomized expression product-containing region could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the variable region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-8R, CD4 and LFA-1.

Useful sequences include sequences from: I) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:8); Nakauchi et al., PNAS USA 82:5126 (1985) and 1–21 in the case of ICAM-2 (MSSFGYRTLTVALFTLICCPG (SEQ ID NO:9); Staunton et al., Nature (London) 339:61 (1989)). These leader sequences deliver the construct to the membrane while the hydrophobic transmembrane domains, placed 3' of the random candidate region, serve to anchor the construct in the membrane. These transmembrane domains are encompassed by amino acids 145–195 from CD8 (PQRPEDCRPRGSVKGTGLDFACDIYIWAPLAGICVA LLLSLIITLICYHSR (SEQ ID NO:10); Nakauchi, supra) and 224–256 from ICAM-2 (MVIIVTVVSVLLSLFVTSVLLCFIFGQHLRQQR (SEQ ID NO:11); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO: 12), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the variable region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:13) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the variable region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQDCCGNCSDSEEELPTRL (SEQ ID NO:14), with the bold cysteines being palmitolyated; Stoffel et al., J. Biol. Chem 269:27791 (1994)); from rhodopsin (KQFRNCMLTSLCCGKNTLGD (SEQ ID NO:15); Barnstable et al., J. Mol. Neurosci. 5(3):207 (1994)); and the p21H-ras 1 protein (LNPPDESGPGCMSCKCVLS (SEQ ID NO:16); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:17); Dice, Ann. N.Y. Acad. Sci. 674:58 (1992); or lysosomal membrane sequences from Lamp-1 (MLIPIAGFFALAGLVLIVLIAYLIGRKRSHAGYQTI (SEQ ID NO:18), Uthayakumar et al., Cell. Mol. Biol. Res. 41:405 (1995)) or Lamp-2 (LVPIAVGAALAGVLILVLLAYFIGLKHHHAGYEQF (SEQ ID NO:19), Konecki et al., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:20); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:21); Schatz, supra); mitochondrial intermembrane space sequences (yeast cytochrome c1; MFSMLSKRWAQRTL-SKSFYSTATGAASKS-GKLTQKLVTAGVAAAGITASTLLYADSLT AEAMTA (SEQ ID NO:22); Schatz, supra) or mitochondrial outer membrane sequences (yeast 70 kD outer membrane protein; MKSFITRNKTAILATVAATG-TAIGAYYYYNQLQQQQQRGKK (SEQ ID NO:23); Schatz, supra).

The target sequences may also be endoplasmic reticulum sequences, including the sequences from calreticulin (KDEL (SEQ ID NO:24); Pelham, Royal Society London Transactions B; 1-10 (1992)) or adenovirus E3/19K protein (LYLSRRSFIDEKKMP (SEQ ID NO:25); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21H-ras 1; LNPPDESGPGCMSCKCVLS (SEQ ID NO:26), with the bold cysteine farnesylated; Capon, supra); geranylgeranylation sequences (for example, protein rab-5A; LTEPTQPTRNQCCSN (SEQ ID NO:27), with the bold cysteines geranylgeranylated; Farnsworth, PNAS USA 91:11963 (1994)); or destruction sequences (cyclin B1; RTALGDIGN (SEQ ID NO:28); Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-randomized expression product region-presentation structure, see FIG. 3. In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (i.e., a stem cell factor capable of causing hematopoietic stem cells to divide and maintain their totipotential), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:29); Villinger et al., J. Immunol. 155:3946 (1995)), growth hormone (MATGSRTSLLLAFGLLCLPWLQEGSAFPT (SEQ ID NO:30); Roskam et al., Nucleic Acids Res. 7:30 (1979)); preproinsulin (MALWMRLLPLLALLALWGPDPAAAFVN (SEQ ID NO:31); Bell et al., Nature 284:26 (1980)); and influenza HA protein (MKAKLLVLLYAFVAGDQI (SEQ ID NO:32); Sekikawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows:

MGLTSQLLPPLFFLLACAGNFVHG (SEQ ID NO:33).

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluorescence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the retroviral construct, via PCR, related techniques, or hybridization.

In a preferred embodiment, the fusion partner is a stability sequence to confer stability to the candidate bioactive agent or the nucleic acid encoding it. Thus, for example, peptides may be stabilized by the incorporation of glycines after the initiation methionine (MG or MGG0), for protection of the peptide to ubiquitination as per Varshavsky's N-End Rule, thus conferring long half-life in the cytoplasm. Similarly, two prolines at the C-terminus impart peptides that are largely resistant to carboxypeptidase action. The presence of two glycines prior to the prolines impart both flexibility and prevent structure initiating events in the di-proline to be propagated into the candidate peptide structure. Thus, preferred stability sequences are as follows:

MG(X)$_n$GGPP (SEQ ID NO:34), where X is any amino acid and n is an integer of at least four.

In one embodiment, the fusion partner is a dimerization sequence. A dimerization sequence allows the non-covalent association of one random peptide to another random peptide, with sufficient affinity to remain associated under normal physiological conditions. This effectively allows small libraries of random peptides (for example, $10^4$) to become large libraries if two peptides per cell are generated which then dimerize, to form an effective library of $10^8$ ($10^4 \times 10^4$). It also allows the formation of longer random peptides, if needed, or more structurally complex random peptide molecules. The dimers may be homo- or heterodimers.

Dimerization sequences may be a single sequence that self-aggregates, or two sequences, each of which is generated in a different retroviral construct. That is, nucleic acids encoding both a first random peptide with dimerization sequence 1, and a second random peptide with dimerization sequence 2, such that upon introduction into a cell and expression of the nucleic acid, dimerization sequence 1 associates with dimerization sequence 2 to form a new random peptide structure.

Suitable dimerization sequences will encompass a wide variety of sequences. Any number of protein—protein interaction sites are known. In addition, dimerization sequences may also be elucidated using standard methods such as the yeast two hybrid system, traditional biochemical affinity binding studies, or even using the present methods.

The fusion partners may be placed anywhere (i.e. N-terminal, C-terminal, internal) in the structure as the biology and activity permits.

In a preferred embodiment, the fusion partner includes a linker or tethering sequence, as generally described in PCT US 97/01019, that can allow the candidate agents to interact with potential targets unhindered. For example, when the candidate bioactive agent is a peptide, useful linkers include glycine-serine polymers (including, for example, $(GS)_n$, $(GSGGS)_n$, (SEQ ID NO:35) and $(GGGS)_n$ (SEQ ID NO:36), where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

In addition, the fusion partners, including presentation structures, may be modified, randomized, and/or matured to alter the presentation orientation of the randomized expression product. For example, determinants at the base of the loop may be modified to slightly modify the internal loop peptide tertiary structure, which maintaining the randomized amino acid sequence.

In a preferred embodiment, combinations of fusion partners are used. Thus, for example, any number of combinations of presentation structures, targeting sequences, rescue sequences, and stability sequences may be used, with or without linker sequences.

Thus, candidate agents can include these components, and may then be used to generate a library of fragments, each containing a different random nucleotide sequence that may encode a different peptide. The ligation products are then transformed into bacteria, such as E. coli, and DNA is prepared from the resulting library, as is generally outlined in Kitamura, PNAS USA 92:9146–9150 (1995), hereby expressly incorporated by reference.

Delivery of the library DNA into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference. Preferred systems include PhiNX-eco and PhiNX-ampho or similar cell lines, disclosed in PCT US97/01019.

In general, the candidate agents are added to the cells under reaction conditions that favor agent-target interactions. Generally, this will be physiological conditions. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away.

Wherein the candidate agents are nucleic acids, methods known in the art such as calcium phosphate, electroporation, and injection may be used to introduce these to the cells. The exocytic stimulus is generally combined with the cells under physiological conditions. Incubations may be performed at any temperature which facilitates optimal activity, typically between 4 and 40° C. Incubation periods are selected for optimum activity, but may also be optimized to facilitate rapid high through put screening.

A variety of other reagents may be included in the assays. These include reagents like salts, neutral proteins, e.g. albumin, detergents, etc which may be used to facilitate optimal protein—protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for exocytosis detection. Washing or rinsing the cells will be done as will be appreciated by those in the art at different times, and may include the use of filtration, and centrifugation. When second labeling moieties are used, they are preferably added after excess non-bound target molecules are removed, in order to reduce non-specific binding; however, under some circumstances, all the components may be added simultaneously.

In a preferred embodiment, the cells are sorted using fluorescent-activated cell sorting (FACS). In general, $K_D$ s of $\leq 1 \mu M$ are preferred, to allow for retention of binding in the presence of the shear forces present in FACS sorting. In a preferred embodiment, the cells are sorted at very high speeds, for example greater than about 5,000 sorting events per sec, with greater than about 10,000 sorting events per sec being preferred, and greater than about 25,000 sorting events per second being particularly preferred, with speeds of greater than about 50,000 to 100,000 being especially preferred.

Cells processed for stimulation and staining are generally taken up on buffer on ice and filtered prior to cytometry. Cells can be analyzed using a FACSCAN (Becton Dickinson Inc., laser line 488 nm) or a Mo-Flo (Cytomation, Inc., laser lines 350 nM broadband (UV), 488 nm, and 647 nm) Cytometer. Cells are sorted, if desired, using the Mo-Flo.

Wherein the cells are analyzed by microscopy, cells post stimulation or staining are generally mounted onto glass slides and coverslipped; these are directly visualized by brightfield and fluorescence microscopy on an inverted microscope (i.e., TE300, Nikon) using standard BFP, FITC, or TRITC (for example) filter sets. Images can also be obtained using an inverted confocal scanning microscope (Zeiss, Inc, Bio-Rad, Inc.) using standard FITC and TRITC (for example) filter sets.

The sorting results in a population of cells having the desired exocytic properties. In a preferred embodiment, the parameters are set to identify at least one candidate bioactive agent that modulates exocytosis.

In a preferred embodiment, the bioactive agent is characterized. This will proceed as will be appreciated by those in the art, and generally includes an analysis of the structure, identity, binding affinity and function of the agent. Generally, once identified, the bioactive agent is resynthesized and combined with the target cell to verify the exocytosis modulation under various conditions and in the presence or absence of other various agents. The bioactive can be prepared in a therapeutically effective amount to modulate exocytosis and combined with a suitable pharmaceutical carrier.

In a preferred embodiment, the cell populations can be subjected to various experimental conditions, with and without the candidate agents, and with and without exocytic stimulation or inhibition. Changes in conditions include but are not limited to changes in pH, temperature, buffer or salt concentration, etc. In a preferred embodiment, the pH is changed, generally by increasing or decreasing the pH, usually by from about 0.5 to about 3 pH units. Alternatively, the temperature is altered, with increases or decreases of from about 5° C. to about 30° C. being preferred. Similarly, the salt concentration may be modified, with increases or decreases of from about 0.1 M to about 2 M being preferred.

It is understood by the skilled artisan that the steps of the assays provided herein can vary in order. It is also understood, however, that while various options (of compounds, properties selected or order of steps) are provided herein, the options are also each provided individually, and can each be individually segregated from the other options provided herein. Moreover, steps which are obvious and known in the art that will increase the sensitivity of the assay are intended to be within the scope of this invention. For example, there may be additionally washing steps, or segregation, isolation steps. Moreover, it is understood that in some cases detection is in the cells, but can also take place in the media, or vice versa.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Population Based Exocytic Enzyme Activity Measurements

Materials: All chemicals were obtained from Sigma Chemical Co. Dyes and glucuronide were obtained from Molecular Probes, Inc. Cell lines MC-9 and RBL-2H3 were obtained from American Type Culture Collection (ATCC). Cell culture reagents were obtained from Fisher Scientific and molecular biology reagents from Clontech Inc.

Cell Culture: MC-9 cells were maintained as suspension cultures in flasks in media consisting of DMEM with L-arginine (116 mg/ml), L-asparagine (36 mg/ml), sodium pyruvate (1 mM), non-essential amino acids (0.1 mM), folic acid (6 mg/ml), 2-mercaptoethanol (0.05 mM), L-glutamine (2 mM), heat inactivated fetal bovine serum (10%), and 10% T-stim conditioned media (Collaborative Research, Inc.). The cells were kept at a density of between 0.25 and $2 \times 10^6$/ml. Experiments were only conducted on cells which were greater than 95% viable as determined by trypan blue exclusion. RBL-2H3 cells were maintained as adherent cultures on uncoated (tissue culture treated) flasks in media consisting of Eagles MEM with 2 mM L-Glutamine and Earl's BSS, 15% heat inactivated fetal bovine serum. The cells were passaged (0.05% trypsin) so that they were not confluent for more than one day.

Exocytosis Stimulation Protocol: Experiments were carried out in modified tyrodes buffer (MT) which consisted of NaCl (137 mM), KCl (2.7 mM), $CaCl_2$ (1.8 mM), $MgCl_2$ (1 mM), Glucose (5.6 mM), Hepes (20 mM, pH 7.4), and bovine serum albumin (0.1%). MC-9 cells were spun at 400×g and the media was aspirated. The cells were then washed with MT, respun/aspirated and taken up in MT at a density of $5\times10^6$ cells /ml. Cells were then treated with either DMSO or ionophore for 30 minutes (or the time was varied if a timecourse). The cells were then pelleted with the supernatant collected for enzymatic analysis; in some cases, the cells then processed for flow cytometry. All stimulations were carried out at 37° C. Stimulations of RBL-2H3 cells were carried out by washing the adherent cells one time in MT and then adding warmed MT (1 ml/$10^6$ cells) containing the stimulus. The cells were incubated at 37° C. for 30 minutes and the supernatant was harvested for further analysis. In some of the examples, (Examples 4–6), the plate bound cells were stained for annexin and then removed from the flask using No-Zyme (Collaborative Research, Inc.) for further processing for flow cytometry. For stimulation of RBL-2H3 cells with antigen crosslinking the cells were incubated overnight with IgE anti-DNP (Sigma Chemical Co.) in complete media at a concentration of 50 ng/ml. The following day they were washed one time in MT and stimulated as described above with the exception that bovine serum albumin coupled to DNP was used as the stimulus at 100 ng/ml.

Population Based Enzyme Assays: Enzyme assays were carried out on cell supernatants and pellets following exocytic stimulation. Cell supernatants were harvested after stimulation, chilled on ice, and the post 5000×g spin supernatant was collected for enzyme activity analysis. Similarly, cell pellets were collected/lysed in MT containing 0.1% triton X-100 and the post 5000×g spin supernatant was collected for enzyme activity analysis. For each analysis 100 $\mu$l of lysate or supernatant was mixed with 100 $\mu$l of reaction buffer (40 mM Citrate, pH 4.5) containing 2 mM substrate (4-methylumbelliferyl $\beta$-D Glucuronide [glucuronidase] or 4-methylumbelliferyl N-acetyl $\beta$-D glucosaminide) [hexosaminidase substrate ] in a solid black 96 well plate (Costar, Inc.) and incubated at 37° C. for 15 minutes. The plate was read on a fluorescence plate reader (Wallac, Inc.) using excitation 380 nm/emission 440 nm filters every 3 minutes for five times to obtain an enzymatic rate; analyses were carried out in triplicate.

Flow Cytometry: Cells processed for stimulation and staining were taken up in MT on ice and filtered through a 100 $\mu$m filter prior to cytometry. Cells were analyzed using a FACSCAN (Becton Dickinson Inc., laser line 458 nm) or a Mo-Flo (Cytomation, Inc., laser lines 350 nM broadband (UV), 488 nm, and 647 nm) Cytometer. Cells were sorted, if desired using the Mo-Flo.

Results: The results are shown in FIG. 1. Enzymatic activity in the cell supernatant was measured for MC9 (A) and RBL 2H3 (B) cells under various conditions. A) MC-9 cells were stimulated in the presence of DMSO (−) or 2 $\mu$m Ionomycin (+) for 30 minutes. The supernatant was collected and analyzed for glucuronidase or hexosaminidase activity. Stimulated release of granule enzymatic activity is evident. B) RBL-2H3 cells were sensitized for 16 hours with varying amounts of IgE anti-DNP and stimulated to exocytose by exposure to increasing amounts of the antigen BSA-DNP. A dose response of both antibody and antigen is evident in the measured supernatant hexosaminidase activity.

Example 2

Mast Cell Exocytic Light Scatter Changes

The cells were prepared as described in Example 1, and light scatter properties were determined.

Results: The results are shown in FIG. 2. Light scatter changes observed on the flow cytometer (side scatter vs. forward scatter) are plotted as bivariate histograms for RBL-2H3 cells (A, D) and MC-9 cells (B, C, E, F). Cells were stimulated with the ionophore A23187 (0.5 ug/ml) and observed at various timepoints [minutes (A, C), 5 minutes (E), 10 minutes (D), and 30 minutes (B, F)]. Time dependent scatter changes are evident in both cell lines with significant changes occuring during the first 10 minutes which represents the major bolus of exocytosis in these cells.

Example 3

Styryl Dyes Detect Mast Cell Exocytosis by FACS

Styrl Dye Straining: The cells were prepared as described above. Styryl dyes (FM1-43 or FM4-64; Molecular Probe s, Inc.) were diluted to a final concentration of 250 mM in MT and were incorporated into the stimulation buffer (see Example 1). After the stimulation protocol the cells were spun down, aspirated and resuspended in fresh ice cold MT. The cells were then ready for analysis in the flow cytometer (see Example 1).

Results: The results are shown in FIG. 3. MC-9 cells were stimulated (blue=DMSO, red=2 $\mu$M ionomycin) in the presence either FM 4-64 (A, B) or FM 1-43 (C,D,E). A) FM 4-64 labeled cells detected in the flow cytometer in fluorescence channel 1. B) FM 4-64 labeled cells detected in the flow cytometer in fluorescence channel 3. C) FM 1-43 labeled cells detected in the flow cytometer in fluorescence channel 1. D) FM 1-43 labeled cells detected in the flow cytometer in fluorescence channel 3. There is a clear stimulation dependent increase of fluorescence intensity with both dyes; FM 4-64 being the most red-shifted and predominantly detected in channel 3 while FM 1-43 is more broadly fluorescent being detected in both channels 1 and 3. E) MC-9 cells were preincubated with varying doses of the PI-3 kinase inhibitor wortmannin (1 $\mu$M-bar1, 100 nM-bar2, 10 nM-bar3, and 0 nM-bars 1 and 2) prior to stimulation with A23187 (0.5 ug/ml, bars 1–4) or DMSO (bar 5) in the presence of FM 1-43. The mean channel shift detected in the flow cytometer in fluorescence channel 1 is plotted as a bar graph. Wortmannin, a known inhibitor of mast cell exocytosis, causes a dose dependent decrease in the FM 1-43 signal indicating that FM 1-43 signal reflects the degree of degranulation in the MC-9 mast cell line.

Example 4

Annexin-V Staining Detects Mast Cell Exocytosis by FACS

Materials: Annexin-V biotin, Annexin-V FITC and streptavidin APC were obtained from Caltag Laboratories. Other materials and methods used herein can be incorporated from the other examples, particularly Example 1.

Annexin-V Staining: Cells post exocytic stimulus were stained with annexin-PITC at a dilution of 1/100 in MT for 10 minutes at room temperature. The cells were then washed one time in MT, taken up in MT and viewed in the flow cytometer or microscope. For indirect labeling, annexin-biotin was added to the MT during the stimulation procedure at a dilution of 1/200. The cells were then pelleted in ice cold MT, spun, aspirated, and taken up in ice cold MT with streptavidin-APC at a dilution of 1/200 and kept on ice for 15 minutes. After pelleting the cells and aspirating the Streptavidin-APC, the cells were resuspended in MT and viewed in the flow cytometer. In some experiments different secondaries were applied such as streptavidin alexa 488 or 594 (Molecular Probes, Inc.) for visualization in the microscope.

Results: The results are shown in FIG. 4. MC-9 cells were stimulated with either DMSO (Figures A and B) or 2 μm ionomycin (Figures C and D) and then stained with both propidium iodide [P1] (Figures A and C) and annexin-V-FITC (Figures B and D). Stimulation with this dose of ionomycin does not compromise the plasma membrane as demonstrated by no significant increase in P1 staining in the exocytosing cells. Degranulation results in a significant increase in annexin binding as seen comparing Figures D and B.

Example 5

Annexin-V-FITC Stains Exocytic Granules in MC-9 Cells Visualized by Confocal Microscopy Microscopy: Cells post stimulation or staining were mounted onto glass slides and coverslipped; these were directly visualized by brighffield and fluorescence microscopy on an inverted microscope (TE300, Nikon) using standard BFP, FITC, or TRITC filter sets. Some images were obtainad using an inverted confocal scanning microscope (Zeiss, Inc, Bio-Rad, Inc.) using standard FITC and TRITC filter sets.

Results: The results are shown in FIG. 5. MC-9 cells were stimulated with 2 μm ionomycin (Figures A, B, C) or DMSO (Figure D), stained with annexin-V-FITC and mounted for confocal microscopy. A and B) Confocal images of a stimulated cells viewed at their midsection; note cell surface labeled granules. C) A stimulated cell visualized near its top; multiple cell surface granules are evident. D) An unstimulated cell visualized at its midsection; all viable unstimulated cells show low annexin binding and no cell surface granular staining.

Example 6

Annexin-V-FITC Stains Exocytic Granules in RBL-2H₃Cells Stimulated with Antigen Crosslinking Except as otherwise stated below, the methods for this example are described in the preceding examples.

Results: The results are shown in FIG. 6. RBL-2H3 cells were sensitized with IgE and stimulated to exocytosis with either MT buffer only (Figure A) or BSA-DNP antigen (100 ng/ml-Figure B) and then stained with annexin-V-FITC. Numerous cell surface granules are stained in the antigen stimulated cells (B) similar to the pattern seen in MC 9-cells. Viable unstimulated cells (A) show negligible annexin-V staining.

Example 7

In Situ Enzymology of Exocytosing Cells Visualized in the FACS

In Situ Enzymology: MC-9 cells were stimulated for exocytosis as described above and then incubated in enyme substrate buffer (BSA free MT, pH 4.3–7.4 range) containing the substrate ELF-97 Glucuronide (250 μM) for 15 minutes at 37° C. The cells were washed one time in MT and then viewed in the microscope or on the flowcytometer. Further methodologies are described in the preceding examples.

Results: The results are shown in FIG. 7. MC-9 cells ware stimulated with DMSO (Figure A) or A23187 (0.5 μg/ml-Figure B and C) and then stained for in situ glucuronidase activity. A) Flow cytometer histogram of ELF-97 detection indicative of cell surface enzymatic precipitate. Very low signal is seen in the DMSO treated cells. B) Flow cytometer histogram of ELF-97 detection indicative of cell surface enzymatic precipitate. A significant increase in signal is seen upon secretory stimulation with ionophore. C) pH profile of the cell surface enzymatic activity. MT buffer, prepared at different pHs, was used to pH profile the signal seen in the flow cytometer. The bar graphs represent the percentage of maximal signal (as measured by mean channel shift in the flow cytomoter) observed. The enzymatic activity is pH dependent with a peak at less than pH 6; this is consistent with enzymatic acitivity derived from an acidic secretory granule.

Example 8

LYSOTRACKER™ Green is Released from Mast Cell Granules Upon Exocytosis and can be Detected by FACS LYSOTRACKER™ Dye Staining: LYSOTRACKER™ dyes (blue, green, and red) were loaded into cells by diluting them to a final concentration of 1 μM in complete media and incubating the cells for 60 minutes at 37° C. in their presence. After loading, the cells were washed two times in MT and then were ready for further analysis or stimulation. Further methodologies are described in the preceding examples.

Results: The results are shown In FIG. 8. MC-9 cells were loaded with LYSOTRACKER™ green for 1 hour and then stimulated with either DMSO (blue line) or ionomycin (2 μM, red line) and viewed in the flow cytometer. Shown is a histogram of fluorescence intensity detected in channel 1; a significant loss of signal is seen in the ionophore stimulated sample as compared to the DMSO control which is reflective of the release of LYSOTRACKER™ green dye from the secretory granules.

Example 9

Multiparameter Analysis—LYSOTRACKER™ Green, Annexin-V-APC, Forward and Side Scatter Except as otherwise described below, the methodologies described in the preceding examples were used.

Results: The results are shown in FIG. 9. MC-9 cells were treated with different doses of ionomycin (0 μM- A, E; 1 μM-B, F, 2 μM- C, G; and 3 μM- D, H) and observed in the flow cytometer with four parameters simultaneously. The cells were loaded with LYSOTRACKER™green for one hour and then stimulated and stained for annexin-VAPC. Figures A–D: Bivariate histograms of side vs. forward light scatter. Note the dose dependent changes in both parameters from left to right as forward scatter increases and side scatter decreases. Figures E–H: Bivariate histograms of annexin-V-APC vs. LYSOTRACKER™ green signals. As exocytosis increases (left to right) annexin signal becomes greater as the LYSOTRACKER™ signal decreases. This reflects the binding of annexin-V to the cell surface granules and the loss of LYSOTRACKER™ from these granules as they are exposed to the extracellular milieu.

Example 10

Multiparameter Analysis—FM 1-43. Annexin-V-APC. Forward and Side Scatter

Except as otherwise noted below, the methodologies described above were used herein.

Results: The results are shown in FIG. 10. MC-9 cells were treated with either DMSO (Figures A and B) or ionomycin (2 μM, Figures C and D) and observed in the flow cytometer with four parameters simultaneously. The cells were stimulated in the presence of FM 1-43 and stained for annexin-V-APC. Figures A and C: Bivariate histograms of side vs. forward light scatter. Note the stimulation dependent changes in both parameters at the 30 minute timepoint. Figures B and D: Bivariate histograms of Annexin-V-APC vs. FM 1-43. Note the stimulation dependent increases in both signals as the cells move to the upper right of the histogram. The changes reflect the binding of annexin-V to the cell surface granules and the simultaneous coupled endocytosis of the FM 1-43 dye into the MC 9 cells.

Example 11

Simultaneous Multiparameter Measurements in the FACS Correlate with Population Based Enzyme Readouts Calcium Signaling Assays: MC-9 or RBL-2H3 cells were washed one time in MT and loaded with the $Ca^{++}$ sensitive probe Fluo-3 (1 μM, Molecular Probes, Inc.) in MT at 37° C. for 20 minutes. The cells were washed one time in warm MT and then stimulated using the protocol described above. The signal due to rise in the intracellular $Ca^{++}$ concentration was visualized using either the flow cytometer (see below), fluorescence microscopy, or read on a fluorescence plate reader (Wallac, Inc.). Loading of the cells was determined by releasing the intracellular dye with MT containing 0.1% triton X-100.

Except as otherwise noted below, the methodologies described above were used herein.

Results: The results are shown in FIG. 11. MC-9 cells were stimulated in the presence of FM 1-43 and annexin-V-APC stained as described in the methods above. At various timepoints after ionomycin stimulation the cells were put on ice and either analyzed by flow cytometry or for enzymatic activity (cell supernatant). The parameters forward scatter, FM 1-43, annexin-V-APC, and hexosaminidase are plotted on the graph relative to the maximal response for each parameter. For calcium signaling, a separate tube of cells was loaded with Fluo-3 and underwent the identical procedure. The timecourses of the cytometry based parameters indicate that they correlate quite well with exocytosis as measured by hexosaminidase release. Forward scatter, in this example, shows an effect which varies both positively and negatively with time.

Example 12

Expression of VAMP-GFP and VAMP-FRET Constructs cDNA Constructs:

VAMP-GFP construct: The rat VAMP-2 cDNA (obtained from R. Scheller, Stanford University) was PCR modified to introduce: (1) a 5' BstXI site encoding a consensus Kozak and glycine insertion (a.a.2) to facilitate expression and in vivo stability, respectively; (2) a serine-glycine linker with a BamHI site at the 3' end. The GFP coding sequence from CdimGFP (Clontech, Inc.) was PCR modified to introduce a 3' BstXI site encoding a stop codon. The VAMP-GFP fusion was constructed by ligating the modified rVAMP and GFP PCR fragments through a common BamHI site in the serine-glycine linker to create an in-frame fusion protein with the following sequence (SEQ ID NO:37):

MGSATAATVPPAAPAGEGGPPAPPPNLTSNRRLQQTQAQVDEVVDIMRVN

VDKVLERDQKLSELDDRADALQAGASQFETSAAKLKRKYWWKNLKMMIIL

GVICAIILIIIIVYFST

*GSGSGSGSGSGP*VSKGEELFTGVVPILVELDGDVNGHKFSVSGEGEGDAT

YGKLTLKFICTTGKLPVPWPTLVTTLTHGVQCFSRYPDHMKQHDFFKSAM

PEGYVQERTIFFKDDGNYKTRAEVKFEGDTLVNRIELKGIDFKEDGNILG

HKLEYNFNSHNVYIMADKQKNGIKVNFKIRHNIEDGSVQLADHYQQNTPI

GDGPVLLPDNHYLSTQSALSKDPNEKRDHMVLLEFVTAAGITLGMDELYK

Z

The VAMP sequence is underlined, the serine-glycine linker is italicized and the GFP sequence is in regular text.

The VAMP-GFP fusion sequence was cloned into the 96.7 retroviral vector with directional BstXI sites to create pVG. The sequence was verified by sequencing in both directions. Proper expression was verified in transfected and infected cells by Western analysis and fluorescence microscopy.

Trp-FRET construct: The GFP coding sequence from cGFP (Clontech, Inc.) was PCR modified to create: (1) a 5' BstXI site encoding a consensus Kozak and glycine insertion (a.a.2) to facilitate expression and in vivo stability, respectively; (2) a 3'-end SacII site encoding Ala228 at the C-terminus. The BFP coding sequence from cBFP (Clontech, Inc.) was PCR modified to create: (1) a 5' BamHI site encoding Ser2; (2) a 3'-end BstXI encoding a stop codon. A SacII-BamHI conversion linker encoding Factor X and tryptase protease cleavage sites, flanked by GSGS spacers (GSGSIEGRLRKQGSGS (positions 229–245 of SEQ ID NO:38)) was used to fuse the GFP and BFP to create an in-frame fusion protein with the following sequence (SEQ ID NO:38):

MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAA*GSGSIEGRLRKQGSGS*KGEELF

TGVVPILVELDGDVNGHKFSVSGEGEGDATYGKLTLKFICTTGKLPVPWP

TLVTTLTHGVQCFSRYPDHMKQHDFFKSAMPEGYVQERTIFFKDDGNYKT

RAEVKFEGDTLVNRIELKGIDFKEDGNILGHKLEYNFNSHNVYIMADKQK

NGIKVNFKIRHNIEDGSVQLADHYQQNTPIGDGPVLLPDNHYLSTQSALS

KDPNEKRDHMVLLEFVTAAGITLGMDELYKZ

The GFP sequence is underlined, the Factor X/tryptase site linker is italicized and the BEP sequence is in regular text.

The VAMP-GFP fusion sequence was cloned into the BamHI and BstXI sites of the retroviral vector 96.7 to create pGX/TB. The sequence was verified by sequencing in both directions. Proper expression was verified in transfected and infected cells by Western analysis and fluorescence microscopy.

The VAMP-GFP encoding sequence was PCR modified to create a 3'-end SacII site encoding Ala228 at the C-terminus. This fragment was cleaved with XhoI and SacII and cloned into the XhoI/SacII sites of pGX/TB to create pVGX/TB (Trp-FRET), encoding the rVAMP-2-BFP-Factor X/Tryptase sites-GFP fusion protein with the following sequence (SEQ ID NO:39):

GSATAATVPPAAPAGEGGPPAPPPNLTSNRRLQQTQAQVDEVVDIMRVNV

DKVLERDQKLSELDDRADALQAGASQFETSAAKLKRKYWWKNLKMMIILG

VICAIILIIIIVYFST*GSGSGSGSGSGSGPV*

SKGEELFTGVVPILVELDGDVNGHKFSVSGEGEGDATYGKLTLKFICTTG

KLPVPWPTLVTTLTHGVQCFSRYPDHMKQHDFFKSAMPEGYVQERTIFFK

DDGNYKTRAEVKFEGDTLVNRIELKGIDFKEDGNILGHKLEYNFNSHNVY

IMADKQKNGIKVNFKIRHNIEDGSVQLADHYQQNTPIGDGPVLLPDNHYL

STQSALSKDPNEKRDHMVLLEFVTAAGSGSIEGRRKLQGSGSKGEELFTG

VVPILVELDGDVNGHKFSVSGEGEGDATYGKLTLKIFCTTGKLPVPWPTL

VTTLTYGVQCFSRYPDHMKQHDFFKSAMPEGYVQERTIFFKDDGNYKTRA

EVKFEGDTLVNRIELKGIDFKEDGNILGHKLEYNYNSHNVYIMADKQKNG

IKVNFKIRHNIEDGSVQLADHYQQNTPIGDGPVLLPDNHYLSTQSALSKD

PNEKRDHMVLLEFVTAAGITLGMDELYKZ

The VAMP sequence is underlined, the serine-glycine linker is italicized, the Factor X/tryptase site linker is in bold and the GFP and BFP sequences are in shown in regular text.

The rVAMP-2-BFP-Factor X/Tryptase sites-GFP fusion sequence was verified by sequencing in both directions. Proper expression was verified in transfected and infected cells by Western and fluorescence microscopy and FACS analysis.

Transfections and Infections: To infect MC-9 and RBL-2H3 cells with recombinant retroviruses expressing the Vamp constructs the following procedure was carried out Phoenix E or A cells (obtained from G. Nolan, Stanford Univ.) were plated out in 6 well plates at 8×10E5 cells in 1.5 ml media (DMEM, 10% FBS) on day one. On day two 5 μg of DNA was transfected into the cells using the $CaPO_4$ precipitation method in the presence of 50 μM chloroquine. The precipitate was incubated with the cells for 8 hours at 37° C. at which time the medium was removed, washed once with fresh media and replaced with either fresh MC-9 or RBL-2H3 media; the cells were then incubated at 32° C. for 48–72 hours. The supernatant from the Phoenix cells (viral supernatant) was spun at 1000×g for 10 minutes and protamine sulfate was added to a final concentration of 5 μg/ml; this supernatant was added to the MC-9 or RBL-2HS freshly trypsinized) cells in a 6 well plate (5×10E5 cells per well) and the mixture was spun at 1000×g for 90 minutes at room temperature The cells were then incubated at 32° C. for 16 hours. The viral supernatant was removed and fresh media was added; target gene expression was seen after 24 hours post infection.

We claim:

1. A method of screening for a bioactive agent which modulates exocytosis in a cell, said method comprising:
   a) combining a candidate bioactive agent and a population of cells;
   b) subjecting said cells to conditions that induce exocytosis in cells of the same type in the absence of said bioactive agent; and
   c) assaying each individual cell to measure at least three properties of said cells, said properties selected from the group consisting of: light scattering, fluorescent dye uptake, fluorescent dye release, granule exposure, annexin granule binding, surface granule enzyme activity, and the quantity of granule specific proteins, wherein said step of assaying is performed using fluorescence activated cell sorting (FACS) by measuring said at least three properties simultaneously or sequentially, and wherein alteration in the at least three assayed properties as compared to cells that were not exposed to the candidate bioactive agent indicates that said agent modulates exocytosis.

2. A method according to claim 1 wherein at least one of said properties is selected from the group consisting of fluorescent dye release, annexin granule binding, surface granule enzyme activity, and the quantity of granule specific proteins.

3. A method according to claim 1 wherein said surface granule enzyme activity is detected by an in situ enzymology assay.

4. A method according to claim 1 wherein said surface granule enzyme activity is detected by a population based enzyme assay.

5. A method according to claim 3 or 4 wherein said assay includes the use of an enzyme substrate coupled to a FRET construct.

6. A method according to claim 1 wherein said granule specific proteins are fusion proteins comprising a granule specific protein and a detectable molecule.

7. A method according to claim 6 wherein said detectable molecule is a FRET construct.

8. A method according to claim 1 wherein the properties selected are light scattering, fluorescent dye uptake and annexin granule binding.

9. A method according to claim 1 wherein the properties selected are light scattering, fluorescent dye uptake and surface granule enzyme activity.

10. A method according to claim 1 wherein the properties selected are light scattering, fluorescent dye uptake and the quantity of granule specific proteins.

11. A method according to claim 1 wherein the properties selected are light scattering, annexin granule binding and the quantity of granule specific proteins.

12. A method according to claim 1 wherein the properties selected are light scattering, annexin granule binding and surface granule enzyme activity.

13. A method according to claim 1 wherein the properties selected are light scattering, the quantity of granule specific proteins and surface granule enzyme activity.

14. A method according to claim 1 wherein the properties selected are fluorescent dye uptake, annexin granule binding and surface granule enzyme activity.

15. A method according to claim 1 wherein the properties selected are fluorescent dye uptake, annexin granule binding and the quantity of granule specific proteins.

16. A method according to claim 1 wherein the properties selected are fluorescent dye uptake, surface granule enzyme activity and the quantity of granule specific proteins.

17. A method according to claim 1 wherein the properties selected are annexin granule binding, surface granule enzyme activity and the quantity of granule specific proteins.

18. A method according to claim 1 wherein the properties selected are light scattering, fluorescent dye uptake and fluorescent dye release.

19. A method according to claim 1 wherein the properties selected are light scattering, fluorescent dye release and annexin binding.

20. A method according to claim 1 wherein the properties selected are light scattering, fluorescent dye release and surface granule enzyme activity.

21. A method according to claim 1 wherein the properties selected are light scattering, fluorescent dye release and the quantity of granule specific proteins.

22. A method according to claim 1 wherein the properties selected are annexin granule binding, fluorescent dye uptake and fluorescent dye release.

23. A method according to claim 1 wherein the properties selected are annexin granule binding, surface granule enzyme activity, and fluorescent dye release.

24. A method according to claim 1 wherein the properties selected are fluorescent dye uptake, the quantity of granule specific proteins and surface granule enzyme activity.

25. A method according to claim 1, further comprising sorting said cells on the basis of said assaying, thereby isolating cells having alterations in said assayed properties.

26. A method according to claim 25, wherein said bioactive agent is a nucleic acid molecule or polypeptide encoded by a vector introduced into said cells.

27. A method according to claim 26, further comprising identifying said bioactive agent in said sorted cells having alterations in said assayed properties.

28. A method according to claim 1, wherein said properties are assayed in individual cells.

29. A method according to claim 1, wherein said cell is selected from the group consisting of: a mast cell, neuron, adrenal chromaffin cell, basophil, endocrine cell, exocrine cells, neutrophil, monocyte, lymphocyte, mammary cell, sperm cell, egg cell, polymononuclear (PMN) cell, endothelial cell, adipocyte, and muscle cell.

30. A method according to claim 1, wherein assaying for fluorescent dye uptake is performed on cells labeled with a fluorescent dye.

31. A method according to claim 30 wherein said fluorescent dye uptake is styryl dye uptake.

32. A method according to claim 1, wherein assaying for fluorescent dye release is performed on cells labeled with a fluorescent dye.

33. A method according to claim 32 wherein said fluorescent dye is a low pH concentration dye.

34. A method according to claim 33 wherein said fluorescent dye is detected in the cells.

35. A method according to claim 1, wherein assaying for granule exposure is performed on cells labeled with detectable annexin, a cationic dye or detectable concanavalin A (Con A).

36. A method according to claim 1, wherein assaying for annexin granule binding is performed on cells labeled with detectable annexin.

* * * * *